US010775362B2

(12) United States Patent
Tateyama et al.

(10) Patent No.: US 10,775,362 B2
(45) Date of Patent: Sep. 15, 2020

(54) URINE ANALYZER AND URINALYSIS METHOD

(71) Applicant: SYSMEX CORPORATION, Kobe-shi, Hyogo (JP)

(72) Inventors: Shota Tateyama, Kobe (JP); Masakazu Fukuda, Kobe (JP); Mitsumasa Sakamoto, Kobe (JP)

(73) Assignee: Sysmex Corporation, Hyogo (JP)

( * ) Notice: Subject to any disclaimer, the term of this patent is extended or adjusted under 35 U.S.C. 154(b) by 206 days.

(21) Appl. No.: 15/992,500

(22) Filed: May 30, 2018

(65) Prior Publication Data

US 2018/0348200 A1 Dec. 6, 2018

(30) Foreign Application Priority Data

May 31, 2017 (JP) ................................ 2017-108806

(51) Int. Cl.

| | |
|---|---|
| ***G01N 33/92*** | (2006.01) |
| ***G01N 33/50*** | (2006.01) |
| ***G01N 33/493*** | (2006.01) |
| ***G01N 15/14*** | (2006.01) |
| *G01N 33/52* | (2006.01) |
| *G01N 33/53* | (2006.01) |
| *G01N 21/956* | (2006.01) |
| *G01N 35/00* | (2006.01) |
| *G01N 15/00* | (2006.01) |

(52) U.S. Cl.

CPC ....... *G01N 33/493* (2013.01); *G01N 15/1434* (2013.01); *G01N 15/1459* (2013.01); *G01N 33/92* (2013.01); *G01N 15/14* (2013.01); *G01N 21/95623* (2013.01); *G01N 2015/0065* (2013.01); *G01N 2035/00465* (2013.01)

(58) Field of Classification Search

CPC ............... G01N 15/14; G01N 15/1434; G01N 15/1459; G01N 2015/0065; G01N 2035/00465; G01N 21/95623; G01N 33/493; G01N 33/92

See application file for complete search history.

(56) References Cited

U.S. PATENT DOCUMENTS

| | | | |
|---|---|---|---|
| 9,417,231 B2 | 8/2016 | Sakamoto et al. | |
| 9,857,361 B2 * | 1/2018 | Wanders ............ | G01N 15/1468 |

(Continued)

FOREIGN PATENT DOCUMENTS

| | | |
|---|---|---|
| EP | 2843409 A1 | 3/2015 |
| EP | 2963418 A1 | 1/2016 |

(Continued)

*Primary Examiner* — Jennifer Wecker
(74) *Attorney, Agent, or Firm* — Brinks Gilson & Lione

(57) ABSTRACT

The urine analyzer 10 includes a sample preparation unit 30 for mixing a urine sample with a hemolytic agent to prepare a measurement sample, a flow cell 41 for flowing a measurement sample, a light source 42 for irradiating light on the measurement sample flowing through the flow cell 41, a light receiving unit 50 for receiving scattered light given off from the measurement sample by irradiation of light and outputting a scattered light signal, and an analysis unit 12 for detecting fat particles in the measurement sample by using a parameter reflecting the intensity of the scattered light signal output by the light receiving unit 50, and a parameter reflecting the width of the scattered light signal.

21 Claims, 15 Drawing Sheets

(56) References Cited

U.S. PATENT DOCUMENTS

| | | | | |
|---|---|---|---|---|
| 2003/0017523 | A1 | 1/2003 | Hotta et al. | |
| 2014/0242633 | A1* | 8/2014 | Fukuda | G01N 33/5094 435/39 |
| 2015/0060647 | A1* | 3/2015 | Sakamoto | G01J 1/0429 250/208.2 |
| 2015/0369741 | A1* | 12/2015 | Ozasa | G01N 33/493 435/6.1 |
| 2016/0061821 | A1* | 3/2016 | Tateyama | G01N 21/49 435/6.1 |

FOREIGN PATENT DOCUMENTS

| | | | |
|---|---|---|---|
| EP | 3112863 | A1 | 1/2017 |
| JP | H10-185803 | | 7/1998 |
| JP | 2015-049066 | | 3/2015 |
| JP | 2016-519760 | | 7/2016 |
| WO | WO 01/059462 | | 8/2001 |

* cited by examiner

FIG. 6A
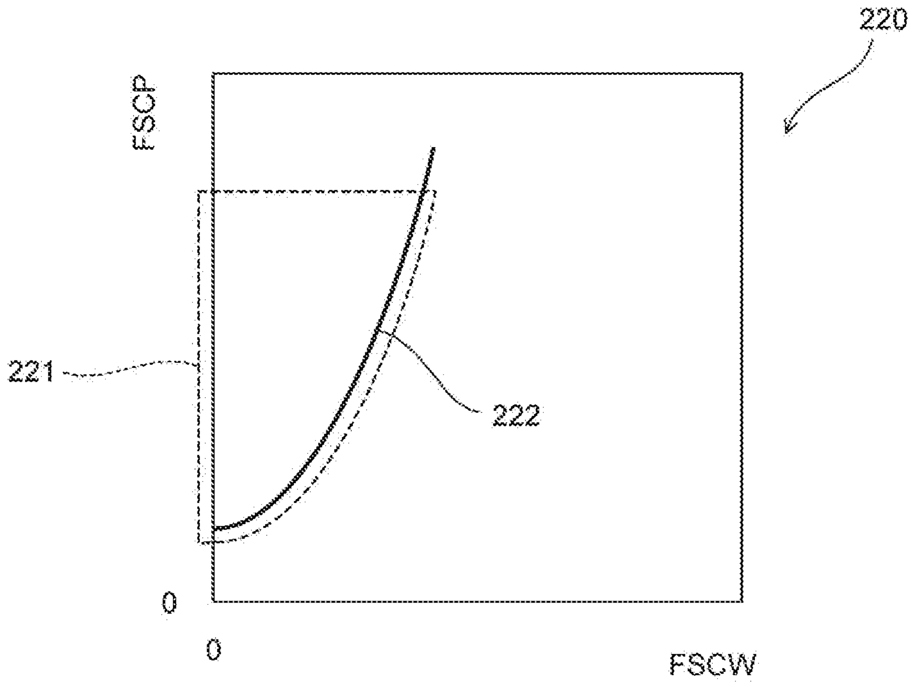
FIG. 6B Modification
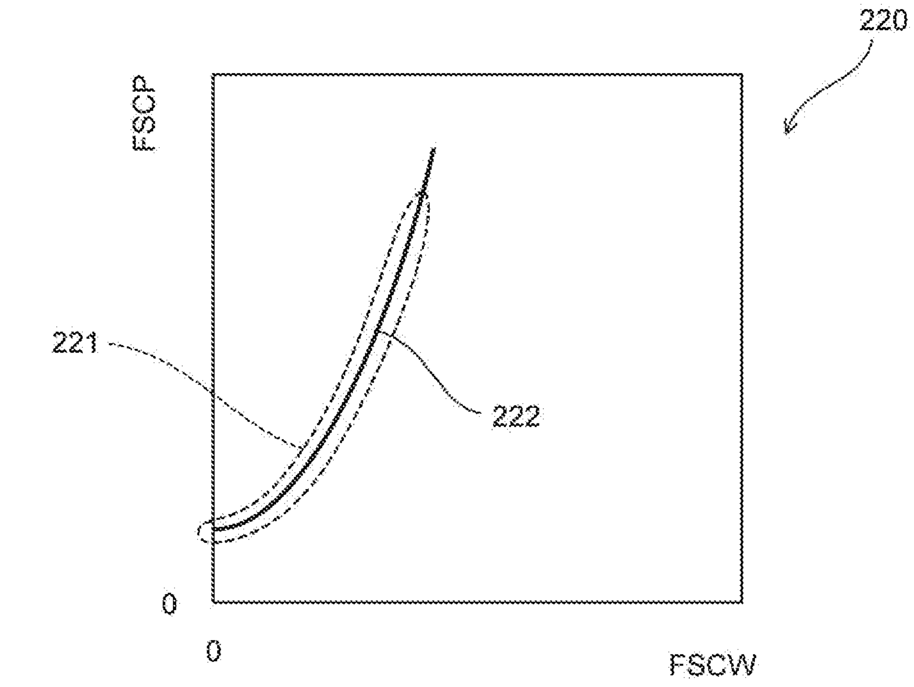

FIG. 9A Fat particles appear, erythrocytes do not appear in urine sample
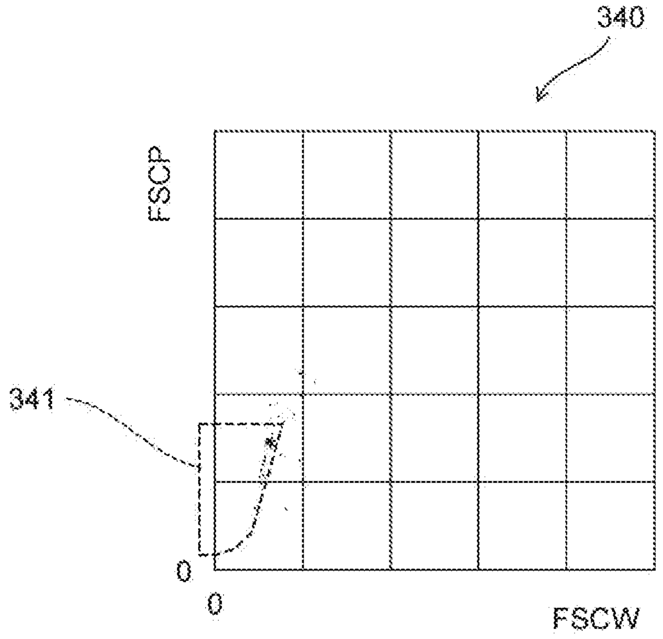
FIG. 9B Fat particles do not appear, erythrocytes appear in urine sample
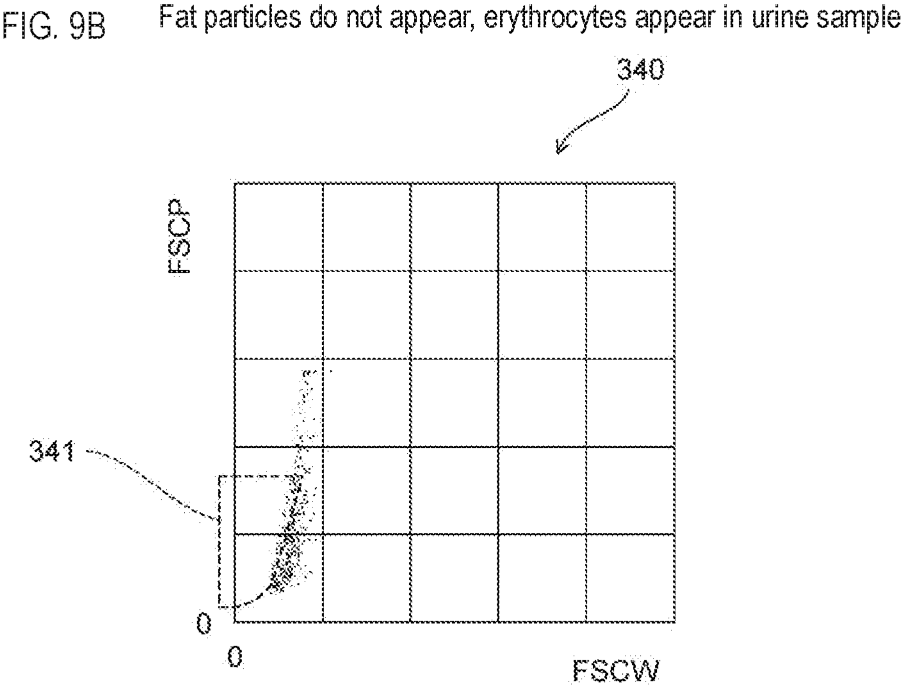

| Item name | | Value | |
|---|---|---|---|
| Erythrocyte | * | ... | /μL |
| Leukocyte | | ... | /μL |
| Epithelial cell | | ... | /μL |
| Squamous epithelial cell | | ... | /μL |
| Tubular epithelial cell | | ... | /μL |
| Cast | | ... | /μL |
| Bacteria | | ... | /μL |
| Fat particle | | ... | /μL |
| Ovoid circular fat body | | ... | /μL |
| Crystal | | ... | /μL |
| Mucous thread | | ... | /μL |
| Heterotypic cell | | ... | /μL |
| Sperm | | ... | /μL |
| Fungus | | ... | /μL |
| Trichomonas | | ... | /μL |

Sample ID: -------
Measurement date: 2017/01/14  10:54:49
Patient ID: -------
Patient name: -------

FIG. 14A

±1 rank coincidence ratio: 35.4%

| | | | | | | |
|---|---|---|---|---|---|---|
| Comparative example | > 15 | 7 | 24 | 12 | 6 | 4 |
| | 11 – 15 | 1 | 30 | 11 | 3 | 1 |
| | 6 – 10 | 1 | 6 | 3 | 1 | 0 |
| | 1 – 5 | 1 | 6 | 3 | 4 | 2 |
| | 0 | 0 | 0 | 1 | 0 | 0 |
| | RBC (/μL) | 0 | 1 - 5 | 6 - 10 | 11 - 15 | > 15 |
| | | Microscope | | | | |

FIG. 14B

±1 rank coincidence ratio: 58.3%

| | | | | | | |
|---|---|---|---|---|---|---|
| Embodiment | > 15 | 2 | 14 | 9 | 5 | 4 |
| | 11 – 15 | 1 | 15 | 9 | 2 | 1 |
| | 6 – 10 | 2 | 12 | 3 | 1 | 0 |
| | 1 – 5 | 1 | 23 | 7 | 5 | 1 |
| | 0 | 4 | 2 | 2 | 1 | 1 |
| | RBC (/μL) | 0 | 1 - 5 | 6 - 10 | 11 - 15 | > 15 |
| | | Microscope | | | | |

FIG. 15A

±1 rank coincidence ratio: 89.5%

| Comparative example RBC (/µL) | Microscope (/HPF) 0 | 1 – 4 | 5 – 9 | 10 – 19 | 20 – 29 | 30 – 49 | 50 – 99 | > 100 |
|---|---|---|---|---|---|---|---|---|
| > 100 | 0 | 0 | 0 | 0 | 0 | 0 | 2 | 14 |
| 50 – 99 | 1 | 1 | 0 | 1 | 1 | 1 | 7 | 3 |
| 30 – 49 | 0 | 0 | 0 | 2 | 4 | 6 | 2 | 0 |
| 20 – 29 | 2 | 0 | 1 | 3 | 3 | 1 | 1 | 0 |
| 10 – 19 | 5 | 0 | 3 | 7 | 4 | 1 | 0 | 0 |
| 5 – 9 | 8 | 10 | 13 | 3 | 2 | 0 | 0 | 0 |
| 1 – 4 | 43 | 31 | 5 | 0 | 0 | 0 | 0 | 0 |
| < 1 | 52 | 5 | 0 | 0 | 0 | 0 | 0 | 0 |

FIG. 15B

±1 rank coincidence ratio: 91.1%

| Embodiment RBC (/µL) | Microscope (/HPF) 0 | 1 – 4 | 5 – 9 | 10 – 19 | 20 – 29 | 30 – 49 | 50 – 99 | > 100 |
|---|---|---|---|---|---|---|---|---|
| > 100 | 0 | 0 | 0 | 0 | 0 | 0 | 2 | 14 |
| 50 – 99 | 1 | 1 | 0 | 1 | 1 | 1 | 7 | 1 |
| 30 – 49 | 0 | 0 | 0 | 2 | 2 | 5 | 2 | 2 |
| 20 – 29 | 0 | 0 | 1 | 3 | 4 | 2 | 1 | 0 |
| 10 – 19 | 4 | 0 | 2 | 6 | 5 | 1 | 0 | 0 |
| 5 – 9 | 5 | 7 | 13 | 4 | 1 | 0 | 0 | 0 |
| 1 – 4 | 38 | 33 | 6 | 0 | 1 | 0 | 0 | 0 |
| < 1 | 63 | 6 | 0 | 0 | 0 | 0 | 0 | 0 |

URINE ANALYZER AND URINALYSIS METHOD

CROSS REFERENCE TO RELATED APPLICATIONS

This application claims priority from prior Japanese Patent Application No. 2017-108806, filed on May 31, 2017, the entire contents of which are incorporated herein by reference.

FIELD OF THE INVENTION

The invention relates to a urine analyzer and a urinalysis method for analyzing a urine-based constituent components.

BACKGROUND

Various diseases can be diagnosed by counting and classifying tangible components in urine. For example, it is known that fat particles, which are fat-containing constituents, appear in the urine of patients suffering from nephrotic syndrome and chronic renal failure. It is possible to identify the possibility that a patient suffers from kidney disease such as nephrotic syndrome or chronic renal failure by analyzing whether fat particles appear in the urine collected from the patient.

WIPO Patent Publication No. 01/059462 discloses a method for measuring fat particles in urine by enzymatic reaction in which fatty particles such as fat droplets, fat bodies and fat globules are uniformly eluted in a urine sample with a surfactant, and an enzyme is caused to act on the eluted fat particles.

SUMMARY OF THE INVENTION

A urine analyzer using a flow cytometry method can be used for analyzing the urine's tangible components. By using a flow cytometric urine analyzer, it is possible to detect various tangible components such as white blood cells, erythrocytes, crystals, casts, fungi, epithelial cells and bacteria in urine. Since fat particles are difficult to stain, however, it was difficult to properly detect fat particles in urine by conventional analysis methods based on the flow cytometry method. In the method of WIPO Patent Publication No. 01/059462, it is necessary to perform a different measurement than flow cytometric measurement in order to execute this technique since fat particles in urine are measured by enzymatic reaction. For this reason, there are necessarily labor and costs incurred when using this method. Therefore, it is desirable to detect fat particles in a flow cytometric urine analyzer.

In view of such problems, the present invention provides a urine analyzer and a urinalysis method capable of detecting fat particles in urine based on a flow cytometry method.

A first aspect of the invention relates to a urine analyzer. The urine analyzer (10) according to this aspect includes a sample preparation unit (30) for mixing a urine sample with a hemolytic agent to prepare a measurement sample, a flow cell (41) for flowing a measurement sample, a light source (42) for irradiating light on the measurement sample flowing through the flow cell (41), a light receiving unit (50) for receiving scattered light given off from the measurement sample by irradiation of light and outputting a scattered light signal, and an analysis unit (12) for detecting fat particles in the measurement sample by using a parameter reflecting the intensity of the scattered light signal output by the light receiving unit (50), and a parameter reflecting the width of the scattered light signal.

The parameter reflecting the intensity of the scattered light signal is a value that reflects the height of the waveform of the scattered light signal. The parameter reflecting the intensity of the scattered light signal is, for example, the peak or the maximum value of the waveform of the scattered light signal from when the scattered light signal exceeds a threshold to when it falls below the threshold. The parameter reflecting the intensity of the scattered light signal only needs to reflect the height of the waveform of the scattered light signal and may be a value half the value of the peak. The parameter reflecting the width of the scattered light signal is a value reflecting the width of the waveform of the scattered light signal. The parameter reflecting the width of the scattered light signal is, for example, the width of the waveform of the scattered light signal indicating an intensity greater than the baseline. The baseline in this case can be set according to various settings in the apparatus. The width of the waveform of the scattered light signal indicates the passage of time while the tangible component measurement target is passing through a known region within the flow cell. In other words, the parameter reflecting the width of the scattered light signal is, for example, the time interval of the waveform of the scattered light signal from when the scattered light signal exceeds the threshold to when it falls below the threshold. Fat particle means an aggregate of fat molecules existing extracellularly, including, for example, fat droplets and fat globules.

According to the urine analyzer of this aspect, detection of red blood cells as fat particles can be suppressed since erythrocytes capable of giving off a scattered light signal similar to fat particles are hemolyzed. Since the fat particles are spherical, a predetermined relationship can be defined between the intensity and the width of the scattered light signals based on fat particles, and fat particles can be properly detected based on this relationship. Since the measurement sample is measured while flowing through the flow cell, the scattered light signal of the fat particles can be properly acquired even if the specific gravity of the fat particles is small, and detection omission of fat particles can be suppressed. Therefore, according to the urine analyzer of this aspect, it is possible to accurately detect fat particles. The detection result of fat particles also can be used for diagnosis of kidney disease and the like.

In the urine analyzer (10) according to this aspect, the light receiving part (50) may be configured to receive forward scattered light as scattered light given off from the measurement sample. Forward scattered light is a concept including not only scattered light generated in the forward direction but also scattered light generated in a direction slightly deviated from the forward direction. Forward scattered light more properly reflects the shape of the fat particles compared to other scattered light that is not forward scattered light. Therefore, fat particles can be properly detected by the forward scattered light.

In the urine analyzer (10) of this aspect, the sample preparation unit (50) is configured to detect fat particles in a measurement sample based on the sample preparation unit (30) further mixing the urine sample with the stain containing the nucleic acid binding dye which binds to the nucleic acid and emits fluorescence by the light from the light source (42), whereupon the light receiving unit (50) receives the fluorescence given off from the measurement sample due to irradiation of light, and the analyzing unit (12) measures the fluorescence received by the light receiving unit (50) on the basis of the fluorescence received by the light receiving unit. Urine samples may also include bacteria such as small yeast-like fungi and unconnected cocci. These yeast-like fungi and bacteria can overlap with fat particles at the values of the two parameters based on scattered light. On the other hand, although these yeast-like fungi and bacteria have nucleic acid to which the nucleic acid binding dyes are bound, fat particles do not have nucleic acids and nucleic acid binding dyes do not bind thereto. Therefore, these yeast-like fungi and bacteria can be excluded from the target of detection of fat particles by further mixing the staining agent containing the nucleic acid binding dye to the urine sample based on the fluorescence from the nucleic acid binding dye. Hence, fat particles can be detected more accurately.

In the urine analyzer (10) according to this aspect, the analysis unit (12) may be configured to count the detected fat particles. The number of fat particles is not limited to the number of fat particles contained in the urine sample or the measurement sample itself, and also includes the number of fat particles per unit volume of the urine sample or the measurement sample.

The urine analyzer (10) according to this aspect includes a stirring unit (21) for stirring the urine sample in the sample container (25), and suction units (22, 23) for suctioning the liquid sample from a container (25) after mixing by the stirring unit (21), and the sample preparation unit (30) can be configured to prepare a measurement sample from the urinary sample suctioned by the suction unit (22, 23). In this case, the fat particles which have a small specific gravity are diffused into the urine sample by the stirring unit, and then the urine sample is suctioned by the suction unit, so that fat particles can be reliably included in the urine sample prepared in the sample preparation unit. Hence, fat particles contained in the urine sample can be detected more accurately.

In the urine analyzer (10) according to this aspect, the sample preparation unit (30) prepares a measurement sample by mixing a hemolytic agent to a part of the urine sample, and simultaneously prepares another measurement sample in which erythrocytes are not hemolyzed from another part of the urine sample; the light receiving unit (50) receives light given off from the other measurement sample flowing through the flow cell (41) and irradiated by light, and the analysis unit (12) detects erythrocytes in the other measurement sample based on the light received from the other measurement sample. In this way it also is possible to detect erythrocytes extremely effectively for determining the possibility of kidney disease.

In this case, the sample preparation unit (30) mixes another part of the urine sample with another stain containing a cell membrane-bound dye which binds to the cell membrane and emits fluorescence by light from the light source (42), such that the light receiving unit (50) receives the fluorescence given off from the other measurement sample due to light irradiation, and the analysis unit (12) detects erythrocytes in the other measurement sample based on the fluorescence received from the other measurement sample by the light receiving section (50). It is possible to remove tangible components other than the solid components combined with crystals and erythrocytes and the like and remove erythrocytes of inappropriate shape on the basis of the fluorescence received from other measurement sample.

In the urine analyzer (10) according to this aspect, the analysis unit (12) is configured to analyze the light received by the light receiving unit (50) from the other measurement sample and the detection result of fat particles obtained from the measurement sample, and count red blood cells in other measurement samples. The detection result of fat particles is, for example, the presence or absence of fat particles and the number of fat particles. Erythrocytes detected on the basis of light received from the other measurement samples may contain fat particles. According to this configuration, however, erythrocytes can be accurately counted from the other measurement samples by using the detection result of fat particles obtained from the measurement sample.

In this case, the light receiving unit (50) receives scattered light given off from the other measurement sample flowing through the flow cell (41) due to light irradiation and outputs a scattered light signal, and the analysis unit (12) is configured to count the erythrocytes in the other measurement sample based on the occurrence range (340) of tangible components including erythrocytes prescribed by a parameter reflecting the intensity of the scattered light signal obtained from the other measurement sample and a parameter reflecting the width of the scattered light signal obtained from the other measurement sample when fat particles have been detected from the measurement sample, and the occurrence range of fat particles (341). The occurrence range of a tangible component including erythrocytes is, for example, a data range for considering a tangible component as erythrocyte, and corresponds to a region set on the scattergram. The occurrence range of fat particles is, for example, a data range for considering a solid component as a fat particle, and corresponds to a region set on the scattergram. According to this configuration, it is possible to distinguish fat particles from erythrocytes, so that it is possible to suppress fat particles from being counted as erythrocytes.

In this case, when fat particles are detected from the measurement sample, the analysis unit (12) is configured to count as erythrocytes in the other measurement sample the tangible components that are included in a range from the occurrence range (340) of tangible components including erythrocytes and excluding the occurrence range (341) of fat particles. When parameters that reflect the intensity and width of the scattered light signal are used, the occurrence range of fat particles overlaps with a part of the occurrence range of the tangible component including erythrocytes. Therefore, when fat particles are present, fat particles may be detected as erythrocytes. In such a case, erythrocytes can be detected more accurately by eliminating the occurrence range of fat particles from the occurrence range of the tangible components including erythrocytes. Since fat particles tend to appear in urine samples collected from patients with kidney disease, false positives also are easily generated in which erythrocyte detection results are positive even though erythrocytes are not mixed in the urine sample. According to this configuration, however, it is possible to suppress false positives in which the detection result of erythrocytes becomes positive in the case of urine samples containing fat particles since the occurrence range of fat particles is excluded from the occurrence range of the tangible components including erythrocytes.

The urine analyzer (10) according to this aspect is provided with a display unit (83); when fat particles are detected from the measurement sample, the analysis unit (12) is configured to display the erythrocyte count result acquired from the other measurement sample and information (621) suggesting the presence of fat particles on the display unit (83). The erythrocyte count result is not limited to the number of erythrocytes contained in the urine sample or other measurement sample itself, and also includes the number of erythrocytes contained per unit volume of the urine sample or other measurement sample. According to this configuration, it is possible to notify the operator that the fat particles have interfered in the detection of erythrocytes.

In the urine analyzer (10) according to this aspect, the light source (42) irradiates linearly polarized light on the measurement sample flowing through the flow cell (41), the light receiving unit (50) receives the depolarized scattered light in which the linearly polarized light is canceled given off from the measurement sample, and the analysis unit (12) detects fat cells in the measurement sample based on the depolarized scattered light received from the measurement sample by the light receiving unit (50). A fat cell means a cell in which a part is denatured to fat or a state in which fat particles have been taken in, for example, an ovoid circular fat body, a fat column and the like. The light receiving unit receives, for example, depolarizing side scattered light based on side scattered light given off in the lateral direction as depolarization scattered light. According to this configuration, fat cells effective for judging the possibility of morbidity to kidney disease can be detected together with fat particles.

In this case, fat cells contain ovoid circular fat bodies. In this way it is possible to detect ovoid circular fat bodies which are effective for determining the possibility of morbidity to nephrotic syndrome or chronic nephritis.

The urine analyzer (10) according to this aspect includes a display unit (83), and the analysis unit (12) can be configured to cause the display unit (83) to display the detection results of the tangible components in the urine sample. The detection result is, for example, the presence or absence of a tangible component to be detected and the counting result. According to this configuration, the operator can perform diagnosis related to kidney disease by referring to the detection result of fat particles. When the detection results of erythrocytes and ovoid fat particles are displayed, the operator can more accurately diagnose kidney disease by referring to these detection results.

A second aspect of the invention relates to a urinalysis method. In the urinalysis method according to this aspect, a hemolytic agent is mixed with a urine sample to prepare a measurement sample (S11), the measurement sample is flowed into the flow cell (41) (S12), scattered light given off due to irradiating the measurement sample flowing through the flow cell (41) is received (S13), and fat particles in the measurement sample are detected using a parameter reflecting the intensity of the scattered light signal corresponding to the received scattered light and a parameter reflecting the width of the scattered light signal (S20).

According to the urinalysis method of this aspect, the same effects as those of the first aspect are obtained.

A third aspect of the invention relates to a urine analyzer. A urine analyzer (10) according to this aspect includes a sample preparation unit (30) for preparing a measurement sample without hemolyzing erythrocytes from a urine sample, a flow cell (41) through which a measurement sample flows, a light source (42) for irradiating the measurement sample flowing through the flow cell (41) with light, a light receiving unit (50) for receiving the scattered light generated from the measurement sample by irradiation with light and outputting a scattered light signal, and an analysis unit (12) for counting as erythrocytes the tangible components included in a range from the occurrence range (340) of the tangible component containing erythrocytes prescribed by a parameter reflecting the intensity of the scattered light signal output by the light receiving unit (50) and a parameter reflecting the width of the scattered light signal, and excluding a range (341) having a predetermined relationship with a parameter reflecting the width of the scattered light signal as erythrocytes.

When the parameters that reflect the intensity and width of the scattered light are used, the occurrence ranges of tangible components other than erythrocytes, such as fat particles, overlap with a part of the occurrence range of the erythrocyte-containing tangible component. Therefore, when other tangible components are present, there is a possibility that other tangible components may be detected as erythrocytes. According to the urine analyzer of this aspect, in such a case, erythrocytes can be detected more accurately by excluding a predetermined occurrence range corresponding to another tangible component from the occurrence range of a tangible component including erythrocytes.

In the urine analyzer (10) according to this aspect, the range (341) in which the parameter reflecting the intensity of the scattered light signal and the parameter reflecting the width of the scattered light signal have a predetermined relationship is within the range where fat particles appear. Since fat particles tend to appear in urine samples collected from patients with kidney disease, false positives also are easily generated in which erythrocyte detection results are positive even though erythrocytes are not mixed in the urine sample. According to the urine analyzer of this aspect, however, the detection result of erythrocytes can be suppressed as a positive false positive when the urine sample contains fat particles since the predetermined occurrence range corresponding to fat particles is excluded from the occurrence range of the tangible components including erythrocytes.

In the urine analyzer (10) according to this aspect, the sample preparation unit (30) prepares a measurement sample from a part of the urine sample, and prepares another measurement sample by mixing hemolytic agent with another part of the urine sample; the light receiving unit (50) receives scattered light given from the other measurement sample flowing through the flow cell (41) due irradiation by light and outputs a scattered light signal, and the analysis unit (12) counts as erythrocytes the tangible components in the occurrence range (340) of tangible components including erythrocytes when a tangible component is not detected in a range in which the parameter reflecting the intensity of the scattered light signal obtained from the other sample and the parameter reflecting the width of the scattered light signal obtained from the other measurement sample have a predetermined relationship. "When a tangible component is not detected" means, for example, a case where the number of tangible components is equal to or less than a predetermined value. In this way, it is determined whether a tangible component, for example, fat particles, which can overlap with the occurrence range of the erythrocyte-containing tangible component based on the measurement sample is present in the urine sample based on the other measurement sample. Then, when a tangible component overlapping with the occurrence range of the erythrocyte-containing tangible component is not detected, the tangible components included in the occurrence range of the erythrocyte-containing tangible component are counted as erythrocytes without excluding the predetermined range. In this way it is possible to suppress an unintentional decrease in the counting result of red blood cells.

A fourth aspect of the invention relates to a urinalysis method. In the urinalysis method according to this aspect, a measurement sample without erythrocyte hemolysis is prepared from the urine sample (S11), the measurement sample is flowed into the flow cell (41) (S12), the measurement sample flowing through the flow cell (41) is irradiated with light which is received (S13), and the tangible components included in a range from the occurrence range (340) of the tangible component containing erythrocytes prescribed by a parameter reflecting the intensity of the scattered light signal output by the light receiving unit (50) and a parameter reflecting the width of the scattered light signal, and excluding a range (341) having a predetermined relationship with a parameter reflecting the width of the scattered light signal are counted as erythrocytes.

According to the urinalysis method of this aspect, the same effects as those of the third embodiment are obtained.

A fifth aspect of the invention relates to a urine analyzer. A urine analyzer (10) according to this aspect includes a sample preparation unit (30) for preparing a measurement sample without hemolyzing erythrocytes from a urine sample, a flow cell (41) through which a measurement sample flows, a light source (42) for irradiating the measurement sample flowing through the flow cell (41) with light, a light receiving unit (50) for receiving the scattered light generated from the measurement sample by irradiation with light and outputting a scattered light signal, and an analysis unit (12) for counting as erythrocytes the tangible components included in a range from the occurrence range (340) of the tangible component containing erythrocytes prescribed by a parameter obtained from the scattered light signals output by the light receiving unit (50) and excluding an occurrence range (341) of fat particles stipulated by a parameter.

According to the urine analyzer of this aspect, the same effect as that of the third aspect is obtained.

A sixth aspect of the invention relates to a urinalysis method. In the urinalysis method according to this aspect, a measurement sample is prepared without erythrocyte hemolysis from the urine sample (S11), the measurement sample is flowed into the flow cell (41) (S12), scattered light given off by the measurement sample flowing through the flow cell (41) due to irradiation with light is received (S13), and tangible components included in a range from the occurrence range (340) of tangible components including erythrocytes prescribed by a parameter obtained from the scattered light signals corresponding to the received scattered light and excluding the occurrence range (341) of fat particles stipulated by a parameter are counted as erythrocytes (S21).

According to the urinalysis method of this aspect, the same effect as that of the fifth aspect are obtained.

According to the invention, fat particles in urine can be detected based on the flow cytometry method.

BRIEF DESCRIPTION OF THE DRAWINGS

FIG. 6A is a diagram schematically showing quadratic curves in which regions set in the scattergram used in the first analysis process according to the embodiment and fat particles are distributed;

FIG. 6B is a diagram schematically showing a modification example of a region set in a scattergram used in the first analysis process according to the embodiment;

FIG. 9A is a diagram showing a scattergram based on a urine sample in which fat particles occur and erythrocytes do not occur, according to the embodiment; FIG. 9B is a diagram showing a scattergram based on a urine sample in which fat particles do not occur and erythrocytes occur according to the embodiment;

FIG. 14A is a diagram showing the number of urine samples in which the rank of the erythrocyte count based on the comparative example coincides with the rank of the erythrocyte count based on the microscopic examination in the verification of the embodiment;

FIG. 14B is a diagram showing the number of urine samples whose rank of the erythrocyte count according to the embodiment matches the rank of the erythrocyte count based on the microscopic examination in the verification of the embodiment;

FIG. 15A is a diagram showing the number of urine samples in which the rank of the erythrocyte count based on the comparative example coincides with the rank of the erythrocyte count based on the microscopic examination in the verification of the embodiment; and FIG. 15B is a diagram showing the number of urine samples in which the rank of the erythrocyte count according to the embodiment matches the rank of the erythrocyte count based on the microscopic examination in the verification of the embodiment.

DETAILED DESCRIPTION OF THE PREFERRED EMBODIMENTS

In the following embodiment, the invention is applied to a flow cytometric urine analyzer for analyzing a tangible component in a urine sample. The tangible component in the urine sample includes fat particles, fat cells, erythrocytes, leukocytes, sperm, fungi, *trichomonas*, epithelial cells, bacteria, casts, mucous yarns, crystals and the like. Fat particle means an aggregate of fat molecules existing extracellularly, including, for example, fat droplets and fat globules. A fat cell means a cell in which a part is denatured to fat or a state in which fat particles have been taken in, for example, an ovoid circular fat body, a fat column and the like. The urine sample to be analyzed includes urine collected from a living body such as urine excreted, urine in the ureter, urine in the bladder, urine in the urethra and the like.

Figure 1:
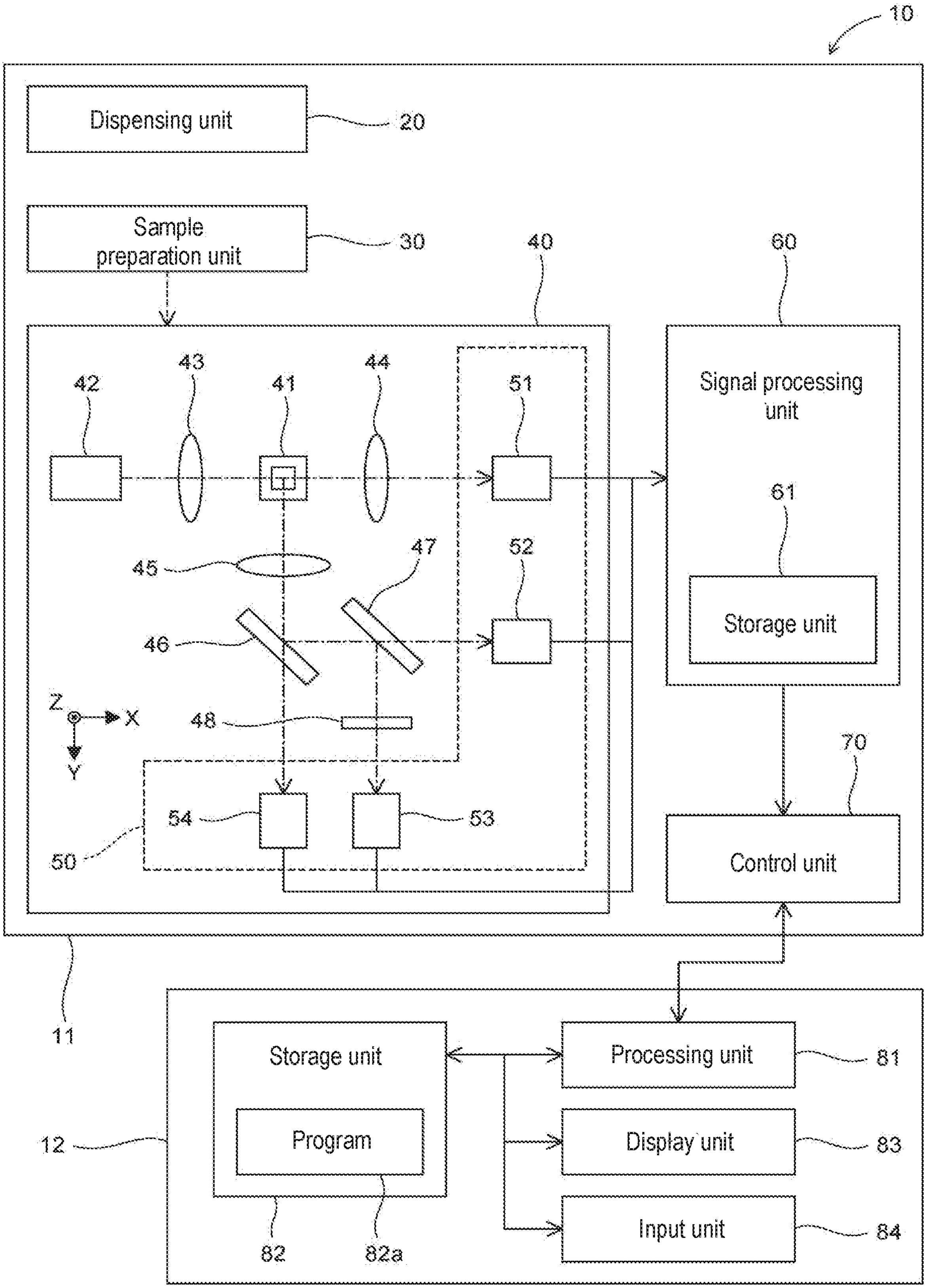
FIG. 1 is a block diagram showing a configuration of a urine analyzer according to an embodiment.

As shown in FIG. 1, the urine analyzer 10 includes a measurement unit 11 and an analysis unit 12. The measurement unit 11 includes a dispensing unit 20, a sample preparation unit 30, an optical detection unit 40, a signal processing unit 60, and a control unit 70. The analysis unit 12 includes a processing unit 81, a storage unit 82, a display unit 83, and an input unit 84. The analyzing unit 12 is configured by, for example, a personal computer.

Figure 2:
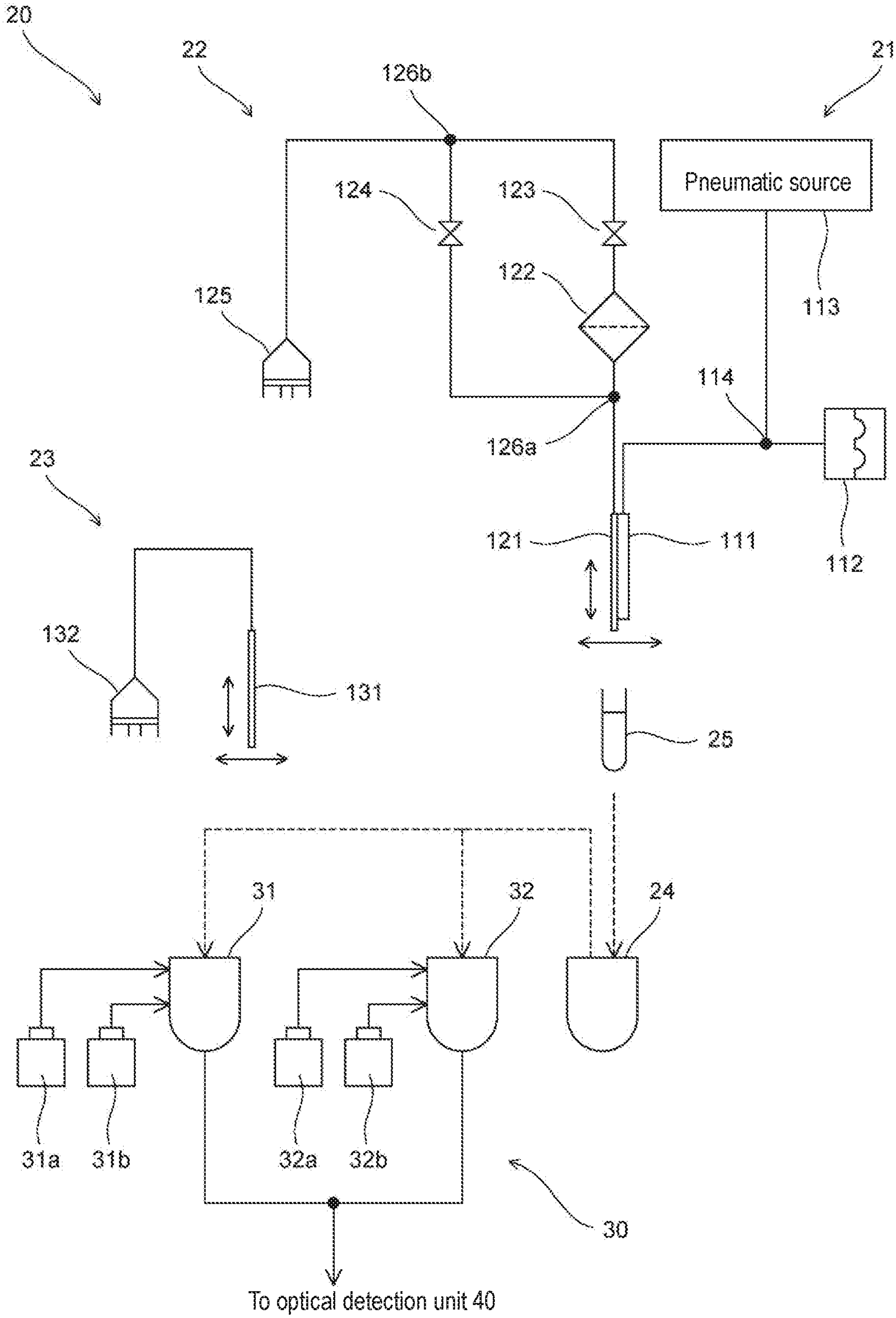
FIG. 2 is a schematic diagram showing a configuration of a dispensing unit and a sample preparation unit according to the embodiment.

As shown in FIG. 2, the dispensing unit 20 includes a stirring unit 21, suction units 22 and 23, and a chamber 24. The stirring unit 21 stirs the urine sample in the sample container 25. The suction units 22 and 23 suction the urine sample from the sample container 25 and dispenses it to the sample preparation unit 30 via the chamber 24.

The stirring unit 21 includes a nozzle 111, a pressure source 112, and a pneumatic source 113. The nozzle 111 and the pressure source 112 are connected by a flow path. The pneumatic source 113 is connected via a flow path to a position 114 on a flow path connecting the nozzle 111 and the pressure source 112. The pressure source 112 is a diaphragm pump. The nozzle 111 is supported by a mechanism (not shown), and can move in the horizontal direction and the vertical direction by this mechanism. Note that the pneumatic source 113 is also used for moving the cleaning liquid and the measurement sample in the measurement unit 11.

The suction unit 22 includes a nozzle 121, a filter 122, valves 123 and 124, and a pressure source 125. The nozzle 121 is installed in a mechanism for moving the nozzle 111 so as to be movable integrally with the nozzle 111. The nozzle 121, the filter 122, the valve 123, and the pressure source 125 are connected in series via a flow path. Both ends of the valve 124 are connected to a position 126*a* on the flow path connecting the nozzle 121 and the filter 122 and a position 126*b* on the flow path connecting the valve 123 and the pressure source 125 via flow paths, respectively. The valves 123 and 124 are electromagnetically opened and closed. The filter 122 is provided with a hole of a diameter through which foreign matter in the urine sample does not pass and a solid component in the urine sample passes. The pressure source 125 is a syringe pump.

Although the nozzle 111 of the stirring unit 21 and the nozzle 121 of the suction unit 22 are configured to be movable integrally, they may be configured to be supported by separate mechanisms so as to be individually movable. The urine sample in the sample container 25 also may be agitated by the suction unit 22, omitting the stirring unit 21.

The suction unit 23 includes a nozzle 131 and a pressure source 132. The nozzle 131 and the pressure source 132 are connected via a flow path. The pressure source 132 is a syringe pump. The nozzle 131 is supported by a mechanism (not shown) and can be moved in the horizontal direction and the vertical direction by this mechanism.

The dispensing operation by the dispensing unit 20 is performed as follows.

When the sample container 25 containing the urine sample is set in the measurement unit 11, the nozzle 111 is inserted into the sample container 25. Then, the urine sample in the sample container 25 is suctioned through the nozzle 111 by the suction pressure generated by the pressure source 112. Thereafter, the urine sample suctioned into the flow path connecting the nozzle 111 and the pressure source 112 is returned to the sample container 25 via the nozzle 111 by the discharge pressure generated by the pressure source 112. In this way, suction and discharge of the urine sample in the sample container 25 is performed by suction and discharge by the nozzle 111. The air supplied from the air pressure source 113 also is discharged into the urine sample of the sample container 25 from the tip of the nozzle 111 via the flow path. In this manner, bubbles are formed in the urine sample in the sample container 25 by the air discharged from the nozzle 111, and the urine sample is agitated. The stirring of the urine sample is completed when the suctioning, discharging, and the bubble stirring with respect to the urine sample are performed a predetermined number of times.

Subsequently, with the valve 123 opened and the valve 124 closed, the nozzle 121 is inserted into the sample container 25. Then, the urine sample in the sample container 25 is suctioned via the nozzle 121 by the suction pressure generated by the pressure source 125. As the suctioned urine sample passes through the filter 122, the foreign matter contained in the suctioned urine sample is captured by the filter 122. Then, after the nozzle 121 is retracted from the sample container 25, the nozzle 121 suctions in air, so that all the suctioned urine sample move toward the pressure source 125 side from the position 126*b*.

Thereafter, with the valve 123 closed and the valve 124 opened, the nozzle 121 is inserted into the chamber 24. Then, the urine sample accommodated in the flow path on the pressure source 125 side of the position 126*b* is discharged from the chamber 24 by the discharge pressure generated by the pressure source 125. Then, the nozzle 121 is retracted from the chamber 24. The urine sample discharged into the chamber 24 by the suction unit 22 is a urine sample in a state where foreign matter has been removed by the filter 122.

Subsequently, the nozzle 131 is inserted into the chamber 24, and the urine sample in the chamber 24 is suctioned through the nozzle 131 by the suction pressure generated by the pressure source 132. Then, the nozzle 131 is inserted into the chamber 31 of the sample preparation unit 30. The urine sample suctioned through the nozzle 131 is discharged into the chamber 31 by the discharge pressure generated by the pressure source 132. Similarly, the nozzle 131 is inserted into the chamber 32 of the sample preparation unit 30. Then, the urine sample suctioned through the nozzle 131 is discharged into the chamber 32 by the discharge pressure generated by the pressure source 132. In this way a part of the urine sample is discharged to the chamber 31, and another part of the urine sample is discharged to the chamber 32. Hereinafter, the urine sample discharged into the chamber 31 will be referred to as a "first portion", and the urine sample discharged into the chamber 32 will be referred to as a "second portion".

As described above, the stirring unit 21 stirs the urine sample in the sample container 25, and the suction units 22 and 23 dispense the stirred urine sample in the sample container 25 to the sample preparation section 30 via the chamber 24 *d*.

The sample preparation unit 30 includes chambers 31 and 32. The sample preparation unit 30 mixes the urine sample dispensed by the suction units 22 and 23 with reagent and prepares two kinds of measurement samples from one urine sample.

A stain solution 31*a* and a diluting liquid 31*b* are connected and can be individually supplied to the chamber 31. In the chamber 31, the first part of the urine sample is mixed with the staining liquid 31*a* and the diluting liquid 31*b*. In this way the tangible component contained in the first portion of the urine sample is stained, and a measurement sample is prepared. Hereinafter, the measurement sample prepared in the chamber 31 is referred to as "first measurement sample".

The staining solution 31*a* is a staining agent containing a nucleic acid binding dye which specifically binds to a nucleic acid. The nucleic acid binding dye emits fluorescence by light from a light source 42 described later. The first measurement sample is used for analysis of cells having nucleic acids such as leukocytes, epithelial cells, sperm, fungus, *trichomonas*, bacteria and the like in urine samples. Hereinafter, particles in a urine sample having a nucleic acid as a basic structure of the particles such as leukocytes, epithelial cells, sperm, fungi, *trichomonas*, bacteria and the like are referred to as "nucleated components". Sperm and bacteria belong to nucleated components because they contain no nucleus but contain nucleic acids.

A dye which is more likely to bind to a nucleic acid than a lipid and a protein is selected as the stain solution 31*a* for staining the nucleated component. More specifically, the staining solution 31*a* contains an intercalator for specifically staining the nucleic acid and a dye binding to the minor groove. Known dyes of cyanine type, acridine type, phenanthridium type can be mentioned as the intercalator. For example, SYBR Green I and Thiazole orange is cited as a cyanine intercalator. Acridin orange can be mentioned as an acridine intercalator. Examples of phenanthridium based intercalators include propidium iodide and ethidium bromide. Examples of the dye to be bonded to the minor groove include known pigments of DAPI and Hoechst. For example, Hoechst 33342 and Hoechst 33258 are examples of dyes that bind to the secondary groove of Hoechet. A cyanine type intercalator is preferable, and SYBR Green I and Thiazole orange are particularly preferable as the staining dye contained in the staining liquid 31*a* of the embodiment.

The diluting liquid 31*b* is a hemolytic agent. The diluting 31*b* contains a cationic surfactant for inducing the passage of the staining solution 31*a* by causing damage to the cell membrane and causing the erythrocytes to hemolyze and condense contaminants such as erythrocyte debris. The diluting liquid 31*b* also may contain a nonionic surfactant rather than a cationic surfactant. The nucleated component is dyed to a degree corresponding to its structure and characteristics by mixing the urine sample, the stain solution 31*a*, and the diluting liquid 31*b*.

Note that the staining liquid 31*a* and the diluting liquid 31*b* are not limited to being separately supplied to the chamber 31, inasmuch as the staining liquid 31*a* and the diluting liquid 31*b* also may be collected as one reagent beforehand and the collected reagent supplied to the chamber 31.

A stain solution 32*a* and a diluting liquid 32*b* are connected to the chamber 32 so as to be separately supplied. A second portion of the urine sample is mixed with staining solution 32*a* and diluting liquid 32*b* in the chamber 32. In this way the tangible component contained in the second portion of the urine sample is stained, and another measurement sample is prepared. Hereinafter, the measurement sample prepared in the chamber 31 is referred to as "second measurement sample".

The stain solution 32*a* is another stain containing a cell membrane and a cell membrane bound dye which binds to the protein. The cell membrane-bound dye emits fluorescence by light from a light source 42 described later. The second measurement sample is used for analysis of particles having no nucleic acid such as erythrocytes, casts, crystals, mucous yarns or the like in the urine sample. Hereinafter, particles in urine samples that do not have nucleic acids as basic structures of particles such as erythrocytes, casts, crystals, mucous yarns are referred to as "non-nuclear components".

A dye which is more likely to bind to the lipid and protein of the cell membrane than the nucleic acid is selected as the staining solution 32*a* for staining the non-nuclear component. A dye which does not affect the morphology of red blood cells among cyanine type, styryl type and acridine type pigment is preferable as such a dye. A fat-soluble carbocyanine dye is preferable, and in particular, indocarbocyanine dye, oxacarbocyanine dye and the like are preferable as the dye for staining the non-nuclear component. Specific indocarbocyanine dyes include DiI (1,1'-dioctadecyl-3,3,3',3'-tetramethylindocarbocyanine perchlorate), DiD (1,1'-dioctadecyl-3,3,3',3'-tetramethylindodicarbocyanine), DiR (1,1'-dioctadecyltetramethyl indotricarbocyanine Iodide) and the like. Examples of the oxacarbocyanine dyes include DiOC 2 (3) (3,3'-diethyloxacarbocyanine iodide), DiOC 3 (3) (3,3-Dipropyloxacarbocyanine iodide), DiOC 4 (3) (3,3'-Dibutyloxacarbocyanine iodide), DiOC 5 3) (3,3-dipentyloxacarbocyanine iodide) and the like. DiOC 3 (3) (3,3-Dipropyloxacarbocyanine iodide) is particularly preferred as the staining dye contained in the staining solution 32*a* of the embodiment.

The diluting liquid 32*b* is a buffer. The diluting liquid 32*b* contains an osmotic pressure compensating agent so that a stable fluorescent signal can be obtained without lysing red blood cells. The osmotic pressure of the diluting liquid 32*b* is adjusted to 100 to 600 mOsm/kg so as to have an osmotic pressure suitable for classification measurement. The cell membrane or protein of the non-nuclear component is stained by mixing the staining solution 32*a*, and the diluting liquid 32*b*.

Note that the staining liquid 32*a* and the diluting liquid 32*b* are not limited to being separately supplied to the chamber 32, inasmuch as the staining liquid 32*a* and the diluting liquid 32*b* also may be collected as one reagent beforehand and the collected reagent supplied the chamber 32.

The chambers 31 and 32 are connected to the flow cell 41 of the optical detection unit 40 via flow paths, respectively. The first measurement sample prepared in the chamber 31 and the second measurement sample prepared in the chamber 32 are supplied to the flow cell 41 via a flow path.

Returning to FIG. 1, the optical detection unit 40 includes a flow cell 41, a light source 42, condenser lenses 43 to 45, a dichroic mirror 46, a half mirror 47, a polarizing filter 48, and a light receiving unit 50. The light receiving unit 50 is configured by photodetectors 51 to 54. The light receiving unit 50 detects light given off from a tangible component in the measurement sample by irradiation of light from the light source 42. The XYZ axes for explaining the arrangement of each part of the optical detection section 40 are shown in FIG. 1. The XYZ axes are orthogonal to each other.

The flow cell 41 allows the first measurement sample and the second measurement sample to flow in the Z-axis direction. The first measurement sample and the second measurement sample form a narrow flow encapsulated in the sheath liquid in the flow cell 41. In this way the tangible components contained in the first measurement sample and the second measurement sample pass through the flow cell 41 one by one.

The light source 42 emits laser light having a wavelength of about 488 nm in the X axis positive direction and irradiates the measurement sample flowing through the flow cell 41 with laser light. The light source 42 is configured by, for example, a semiconductor laser light source or a gas laser light source. The laser beam emitted from the light source 42 is linearly polarized light. The light source 42 is installed in the measurement unit 11 so that the polarization direction of the linearly polarized light is parallel to the flow direction of the measurement sample in the flow cell 41, that is, parallel to the Z axis direction. In other words, the polarization direction of the laser beam emitted from the light source 42 is perpendicular to the incident plane when the plane perpendicular to the Z axis direction is the incident plane.

The condenser lens 43 condenses the laser light emitted from the light source 42 on the measurement sample flowing through the flow cell 41. When the laser light irradiates the measurement sample, forward scattered light, side scattered light and fluorescence are generated from the tangible components passing through the region irradiated with the laser light.

The condenser lens 44 focuses the forward scattered light generated in the X axis positive direction of the flow cell 41 on the photodetector 51. The photodetector 51 receives the forward scattered light and outputs a detection signal corresponding to the intensity of the received forward scattered light. The detection signal corresponding to the intensity of the forward scattered light, that is, a forward scattered light signal, is hereinafter referred to as "FSC". The photodetector 51 is configured by, for example, a photodiode.

The condenser lens 45 condenses the side scattered light and the fluorescence generated in the Y axis positive direction of the flow cell 41 on the dichroic mirror 46. The dichroic mirror 46 reflects the side scattered light and transmits the fluorescence. The non-polarization type half mirror 47 divides the side scattered light reflected by the dichroic mirror 46 into two parts. The photodetector 52 receives the side scattered light transmitted through the half mirror 47 and outputs a detection signal corresponding to the intensity of the received side scattered light. The detection signal corresponding to the intensity of the side scattered light, that is, the side scattered light signal is hereinafter referred to as "SSC". The photodetector 52 is configured by, for example, a photomultiplier. The side scattered light reflected by the half mirror 47 is incident on the polarizing filter 48.

The polarizing filter 48 blocks light in a polarization direction parallel to the Z axis direction and passes light in a polarization direction parallel to the X axis direction. The side scattered light that has passed through the polarizing filter 48 is hereinafter referred to as "depolarization side scattered light". The photodetector 53 receives the depolarized side scattered light and outputs a detection signal corresponding to the intensity of the received depolarized side scattered light. The detection signal corresponding to the intensity of the depolarization side scattered light, that is, the depolarization side scattered light signal, is hereinafter referred to as "DSSC". The photodetector 53 is configured by, for example, a photomultiplier.

Here, when the laser light is irradiated on the tangible component in the measurement sample, the polarization direction of the laser light at the portion where the component is distributed changes in accordance with the optical rotation possessed by the component included in the tangible component. When the polarization direction of the laser light applied to the measurement sample partially changes, the side scattered light includes light components of various polarization states. Among the side scattered light generated in the Y axis positive direction from the tangible component, the proportion of the light component in the polarization direction parallel to the X axis direction, that is, the degree to which the initial polarization direction parallel to the Z axis direction is destroyed, is determined according to the components contained in the tangible component. Therefore, the amount of depolarized side scattered light that passes through the polarizing filter 48 and reaches the photodetector 53 varies depending on the type of the tangible component.

The photodetector 54 receives the fluorescence transmitted through the dichroic mirror 46 and outputs a detection signal corresponding to the intensity of the received fluorescence. A detection signal corresponding to the intensity of fluorescence, that is, a fluorescence signal, is hereinafter referred to as "FL". The photodetector 54 is configured by, for example, a photomultiplier.

Note that forward scattered light is a concept including not only the scattered light generated in the forward direction of the X axis positive direction but also the scattered light generated in the direction slightly deviated from the forward direction. Therefore, forward scattered light detected by the photodetector 51 is not necessarily scattered light generated in the forward direction of the flow cell 41, and also may be scattered light generated in a direction slightly shifted from the forward direction of the flow cell 41. Similarly, side scattered light is a concept including not only the scattered light generated in the direction perpendicular to the X axis which is the lateral direction, and also may be scattered light generated in the direction slightly deviated from the lateral direction. Therefore, side scattered light detected by the photodetector 52 is not necessarily scattered light generated in the lateral direction of the flow cell 41, and also may be scattered light generated in a direction slightly shifted from the lateral direction of the flow cell 41.

The photodetectors 51 to 54 are configured so that the light receiving sensitivity can be switched between high sensitivity and low sensitivity by the control unit 70. Each of the photodetectors 51 to 54 outputs FSC, SSC, and FL at the light receiving sensitivity set by the control unit 70.

An amplifier circuit (not shown) is provided at a later stage of the photodetectors 51 to 54. The amplifier circuit includes an FSC amplifier for amplifying the FSC, an SSC amplifier for amplifying the SSC, an FLH amplifier for amplifying the FL at a high amplification factor, and an FLL amplifier for amplifying the FL at a low amplification rate. The gain of each amplifier is configured to be settable in three stages of low level, middle level, and high level by the control unit 70. The FL input to the FLH amplifier is hereinafter referred to as "FLH", and the FL input to the FLL amplifier is hereinafter referred to as "FLU". The FSC, SSC, FLH, FLL signals amplified by the amplifiers of the amplifier circuit are converted into digital signals by an A/D converter (not shown) provided at later stage of the amplifier circuit and input to the signal processing unit 60.

The signal processing unit 60 is composed of a plurality of circuits for processing signals and a storage unit 61. The storage unit 61 is composed of, for example, a RAM. The signal processing unit 60 calculates a plurality of parameters to be used for analysis based on the input FSC, SSC, FLH, FLL waveforms. More specifically, the signal processing unit 60 performs predetermined signal processing on each signal, and calculates parameters such as peak value, width, and area of each signal waveform for each tangible component. The signal processing unit 60 stores the calculated parameters in the storage unit 61.

Figure 3A:
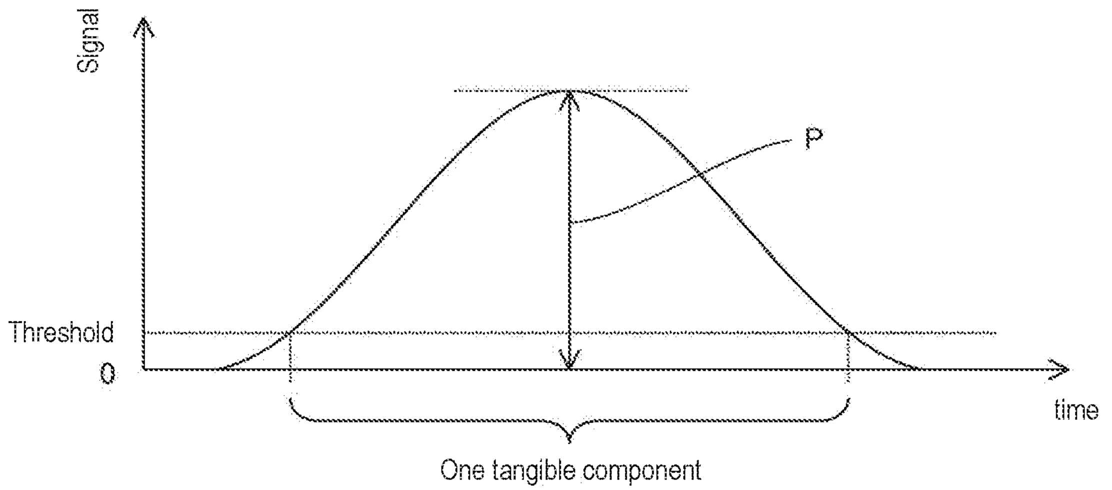
FIG. 3A is a schematic diagram showing peak values of signal waveforms based on one of the tangible components according to the embodiment.

As shown in FIG. 3A, the magnitudes of the FSC, SSC, FLH, and FLL signals change in a pulsed manner in response to passage of the solid component through the region of the flow cell 41 irradiated by the laser light. Therefore, the shape of the signal waveform varies with elapsed time. The waveform of the signal from the time when the signal exceeds the threshold to the time when the signal falls below the threshold, that is, the waveform of the signal showing the intensity greater than the baseline, is regarded as a signal waveform based on one tangible component. The baseline can be set according to various settings and the like in the urine analyzer 10.

Figure 3B:
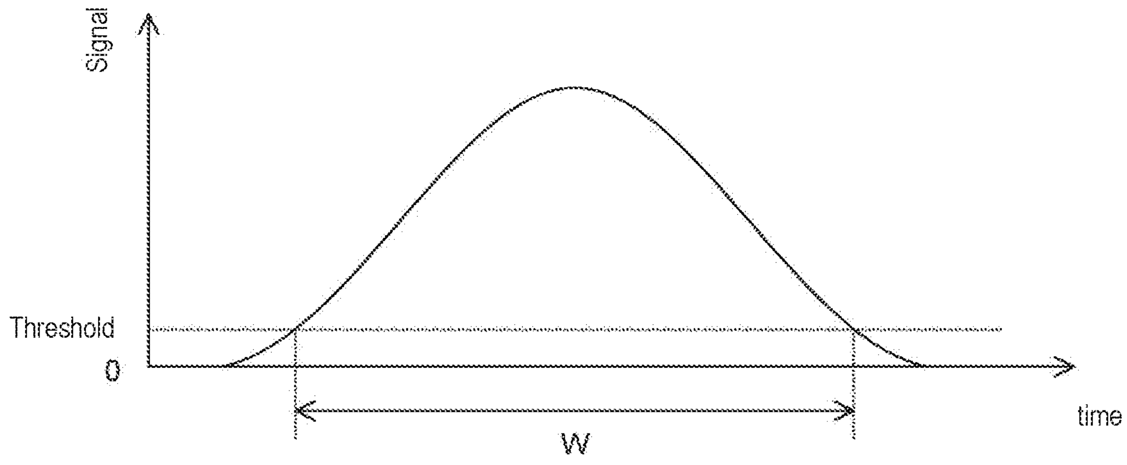
FIG. 3B is a schematic diagram showing the width of a signal waveform based on one solid component according to the embodiment.
Figure 3C:
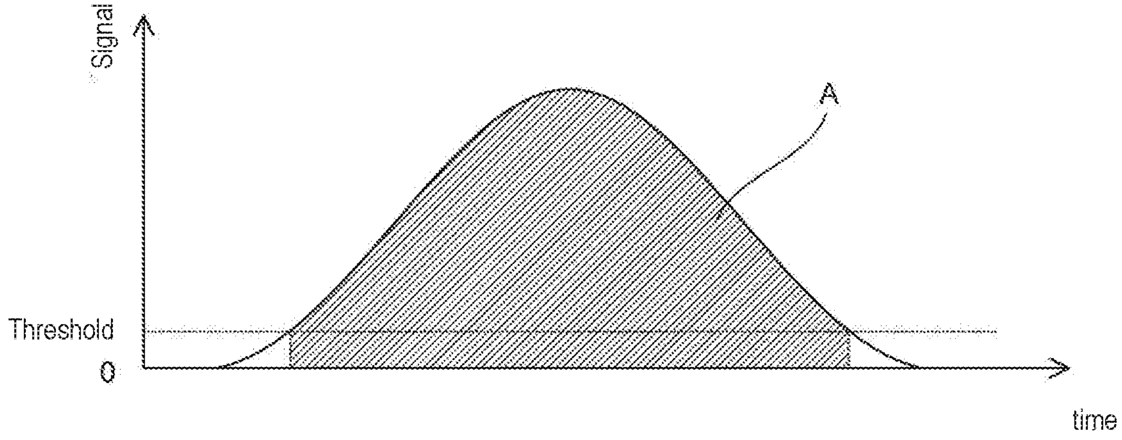
FIG. 3C is a schematic diagram showing an area of a signal waveform based on one piece of a component according to the embodiment.

The peak value P is a parameter that reflects the intensity of the signal. The parameter reflecting the intensity of the signal is a value reflecting the height of the waveform of the signal. Specifically, as shown in FIG. 3A, the peak value P is a peak, that is, a maximum value of a signal waveform from when the signal exceeds the threshold to when it falls below the threshold. The width W is a parameter that reflects the width of the signal. The parameter reflecting the width of the signal is a value reflecting the width of the waveform of the signal. Specifically, the width W is the width of the waveform of the signal showing the intensity greater than the baseline. The width of the waveform of the signal indicates the transit time while the tangible component to be measured passes through the sensing area in the flow cell 41. In other words, as shown in FIG. 3B, the width W is the time interval of the signal waveform from when the signal exceeds the threshold to when it falls below the threshold. The area A is a parameter that reflects the area of the signal, specifically, as shown in FIG. 3C, it is the integrated value of the signal waveform from when the signal exceeds the threshold to when it falls below the threshold.

Note that the method of calculating the parameters is not limited to the above method. For example, the peak value P may be a value reflecting the maximum value of the signal waveform, such as a value obtained by multiplying or adding a maximum value of the signal waveform by a predetermined value. The width W may be a value reflecting the time interval of the signal waveform, such as a value obtained by multiplying or adding a predetermined value to the time interval of the signal waveform. The area A may be a value reflecting the integrated value of the signal waveform, such as the area of a triangle obtained from the peak value P and the width W.

In the following description, the peak value and the width calculated from the waveform of the FSC based on the forward scattered light are referred to as FSCP and FSCW, respectively. The peak value and width calculated from the SSC waveform based on the side scattered light are referred to as SSCP and SSCW, respectively. The peak value and area calculated from the DSSC waveform based on depolarized side scattered light are referred to as DSSCP and DSSCA. The peak value calculated from the FLH waveform based on fluorescence is referred to as FLHP. The width and area calculated from the waveform of FLL based on fluorescence are referred to as FLLW and FLLA, respectively.

Returning to FIG. 1, the control unit 70 receives signals from each unit of the measuring unit 11 and controls each unit of the measuring unit 11. The control unit 70 is configured by a microcomputer. The control unit 70 is communicably connected to the processing unit 81 of the analyzing unit 12. The control unit 70 transmits a plurality of parameters for each of the tangible components based on the first measurement sample and the second measurement sample acquired by the signal processing unit 60, to the processing unit 81 as measurement data.

The processing unit 81 receives signals from each unit of the analysis unit 12 and controls each unit of the analysis unit 12. The processing unit 81 is configured by a CPU. The storage unit 82 is configured with a RAM, a ROM, a hard disk, and the like. The storage unit 82 stores in advance a program 82*a* for analyzing and counting tangible components. The processing unit 81 stores the measurement data received from the control unit 70 in the storage unit 82. By executing the program 82*a*, the processing unit 81 classifies and counts the tangible components in the urine sample based on the measurement data stored in the storage unit 82.

The display unit 83 is configured by a display, and displays information such as a classification result and a counting result by the processing unit 81. The input unit 84 is configured by a mouse and a keyboard. The operator inputs an instruction to the urine analyzer 10 via the input unit 84.

Next, measurement processing and analysis processing by the urine analyzer 10 will be described with reference to FIG. 4. Steps S11 to S19 are measurement processing, and steps S20 to S23 are analysis processing.

In step S11, the control unit 70 controls the dispensing unit 20 and the sample preparation unit 30 to prepare a first measurement sample and a second measurement sample from one urine sample. At this time, the stirring unit 21 agitates the urine sample, and after stirring the urine sample by the stirring unit 21, the urine sample is suctioned by the suction units 22 and 23, and the urine sample is dispensed to the sample preparation unit 30, as described with reference to FIG. 2. When stirring and dispensing are carried out in this manner, the urine sample is suctioned by the suction unit 22 after fat particles of a small specific gravity are diffused into the urine sample by the stirring unit 21. In this way it possible to reliably include fat particles in the urine sample dispensed to the sample preparation section 30, so that fat particles can be reliably measured in the measurement of the first measurement sample. Hence, it is possible to accurately detect fat particles contained in the urine sample in the first analysis process described later.

In step S12, the control unit 70 controls the sample preparation unit 30 and the optical detection unit 40 to flow the first measurement sample to the flow cell 41, controls the light source 42 to irradiate light on the first measurement sample flowing through the flow cell 41. As described above, the first measurement sample is a measurement sample prepared from the first portion of the urine sample, and erythrocytes are hemolyzed in the first measurement sample.

In step S13, the control unit 70 controls the light receiving sensitivity of the photodetectors 51 to 54 and the gain of each amplifier of the amplifier circuit provided in the latter stage of the photodetectors 51 to 54 to set values corresponding to the measurement of the nucleated component excluding bacteria. For example, the light receiving sensitivity of the photodetectors 51 to 54 is set to a low sensitivity, the gain of the FSC amplifier is set to a low level, the gain of the FLL amplifier is set to a low level, the gain of the FLH amplifier is set to the middle level. Each signal based on the light generated from the tangible components included in the first measurement sample is amplified and input to the signal processing unit 60 according to the amplification factor determined by the light receiving sensitivity and the gain.

In step S14, the control unit 70 controls the signal processing unit 60 to calculate a plurality of parameters for each tangible component based on each signal input to the signal processing unit 60. Parameters acquired here are used to detect fat particles, ovoid circular fat bodies, leukocytes, epithelial cells, squamous epithelial cells, Tubular epithelial cells, heterotypic cells, sperm, fungus, *trichomonas*. The signal processing unit 60 stores the calculated parameters in the storage unit 61.

Then, in step S15, the control unit 70 sets the light receiving sensitivities of the photodetectors 51 to 54, and the gains of the respective amplifiers of the amplifier circuits provided at the later stage of the photodetectors 51 to 54 to values corresponding to measurement of bacteria. For example, the light receiving sensitivity of the photodetectors 51 to 54 is set to high sensitivity, the level of the FSC amplifier is set to high level, and the gain of the FLH amplifier is set to high level. Also in this case, each signal based on the light generated from the tangible components contained in the first measurement sample is amplified according to the amplification factor determined by the light receiving sensitivity and the gain, and input to the signal processing unit 60. Note that in this case the amplification factors for FSC and FLH are higher than the amplification factors for FSC and FLH, respectively, relative to the settings in step S13. This is because bacteria are smaller in size and smaller in the amount of fluorescence than other nucleated components.

In step S16, the control unit 70 controls the signal processing unit 60 to calculate a plurality of parameters for each tangible component based on each signal input to the signal processing unit 60. The parameters obtained here are used for detection of bacteria. The signal processing unit 60 stores the calculated parameters in the storage unit 61.

Similarly, the control unit 70 calculates a plurality of parameters for each tangible component based on the second measurement sample. That is, in step S17, the control unit 70 controls the sample preparation unit 30 and the optical detection unit 40 to flow the second measurement sample to the flow cell 41, and controls the light source 42 to irradiate light on the second measurement sample flowing in the flow cell 41. As described above, the second measurement sample is a measurement sample prepared from the second portion of the urine sample, and the red blood cells are not hemolyzed in the second measurement sample.

In step S18, the control unit 70 sets the light receiving sensitivities of the photodetectors 51 to 54 and the gains of the respective amplifiers of the amplifier circuits provided in the latter stages of the photodetectors 51 to 54 to values corresponding to the measurement of the non-nuclear component. For example, the light receiving sensitivity of the photodetectors 51 to 54 is set to low sensitivity, the gain of the FSC amplifier is set to the middle level, the gain of the FLL amplifier is set to the middle level, the gain of the FLH amplifier is set to the low level. Each signal based on the light generated from the tangible component included in the second measurement sample is amplified and input to the signal processing unit 60 according to the amplification factor determined by the light receiving sensitivity and the gain.

In step S19, the control unit 70 controls the signal processing unit 60 to calculate a plurality of parameters for each tangible component based on each signal input to the signal processing unit 60. Parameters acquired here are used for detecting erythrocytes, casts, crystals, mucous threads. The signal processing unit 60 stores the calculated parameters in the storage unit 61.

Then, the control unit 70 transmits a plurality of parameters for each tangible component stored in the storage unit 61 in steps S14, S16, and S19 to the processing unit 81 of the analysis unit 12 as measurement data obtained from the same urine sample. The processing unit 81 stores the received measurement data in the storage unit 82.

In step S20, the processing unit 81 executes the first analysis process by executing the program 82*a*. In the first analysis process, the processing unit 81 reads a plurality of parameters for each of the tangible components calculated in step S14 from the storage unit 82, and detects fat particles based on the read parameters. Details of the first analysis process will be described later with reference to FIG. 5A.

In step S21, the processing unit 81 executes the second analysis process by executing the program 82*a*. In the second analysis process, the processing unit 81 reads a plurality of parameters for each of the tangible components calculated in step S19 from the storage unit 82, and detects red blood cells based on the read parameters. Details of the second analysis process will be described later with reference to FIG. 7.

In step S22, the processing unit 81 executes the third analysis process by executing the program 82*a*. In the third analysis process, the processing unit 81 reads a plurality of parameters for each of the tangible components calculated in step S14 from the storage unit 82, and determines the ovoid circular fat bodies, squamous epithelial cells, tubular epithelial cells based on the read parameter. Details of the third analysis process will be described later with reference to FIG. 10A.

In step S23, the processing unit 81 executes the fourth analysis process by executing the program 82*a*. In the fourth analysis process, the processing unit 81 reads a plurality of parameters for each of the tangible components calculated in the steps S14, S16, and S19 from the storage unit 82, and the processing unit 81 detects crystals, casts, a mucous threads, heterotypic cells, leukocytes, epithelial cells, sperm, fungi, *trichomonas*, and bacteria based on the read parameters. Details of the fourth analysis process will be described later with reference to FIGS. 11A to 11E.

Figure 5A:
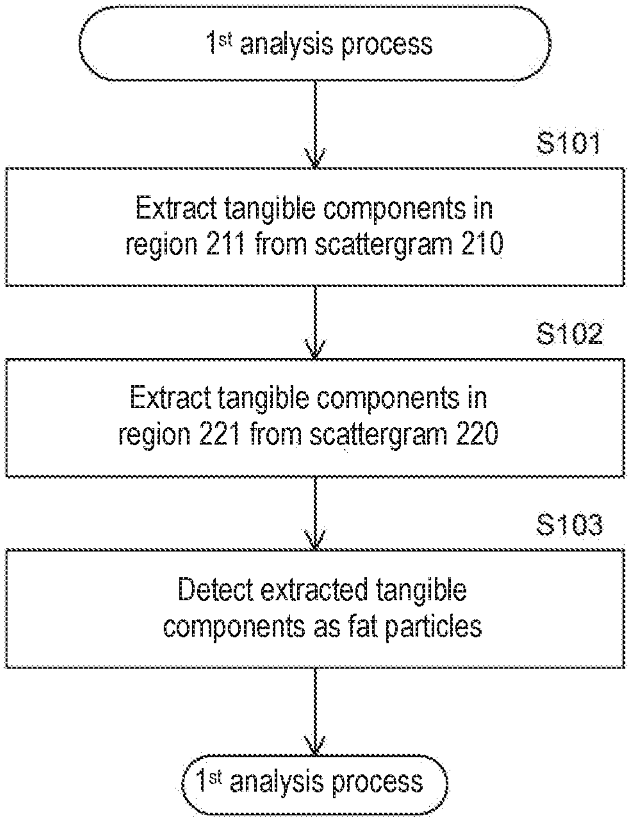
FIG. 5A is a flowchart showing a first analysis process according to the embodiment.

The first analysis process will be described with reference to FIG. 5A.

Figure 4:
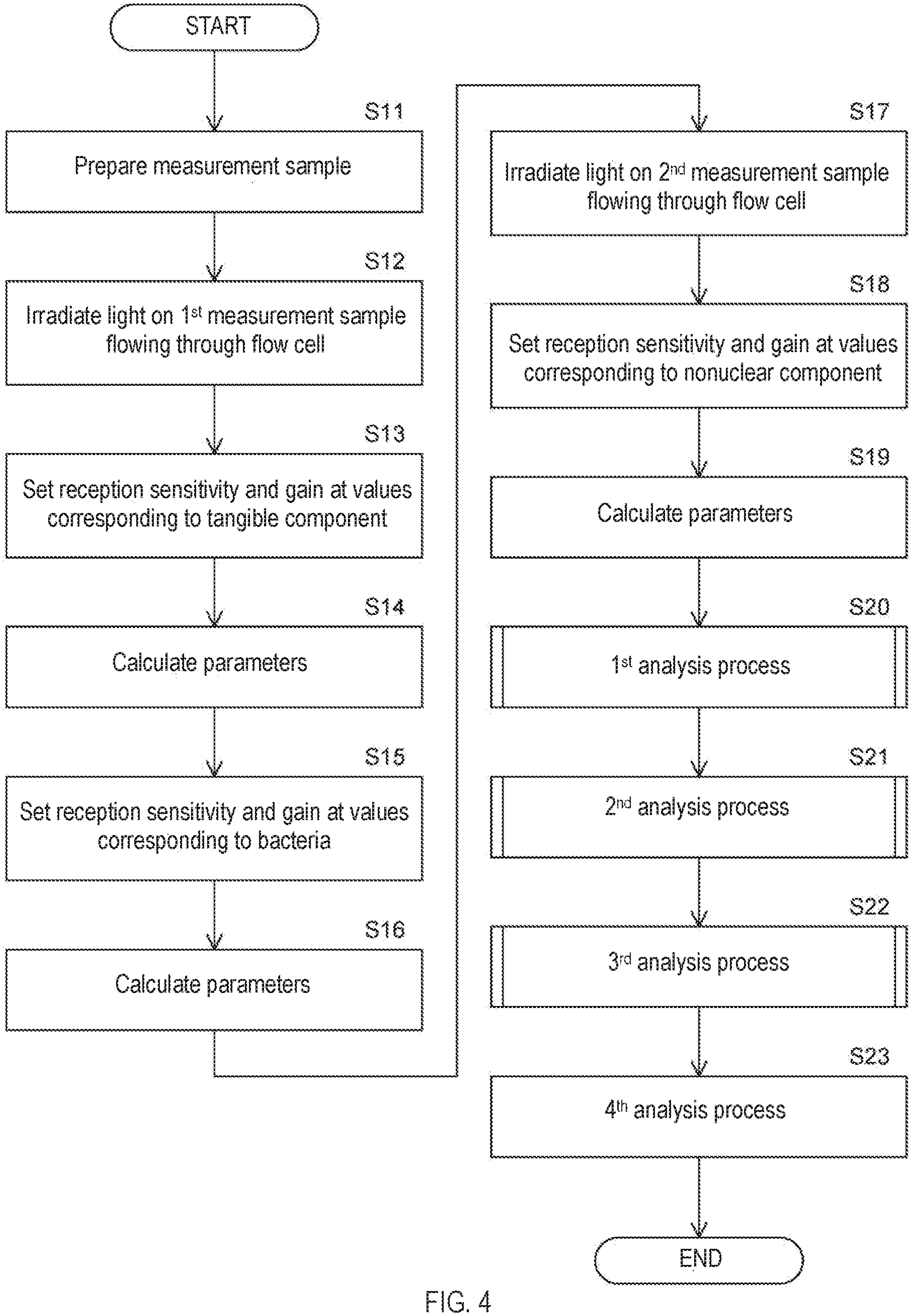
FIG. 4 is a flowchart showing measurement processing and analysis processing by the urine analyzer according to the embodiment.
Figure 5B:
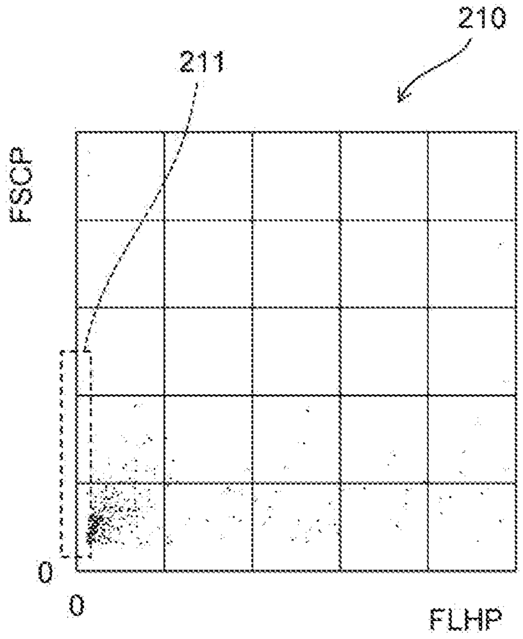
FIG. 5B and FIG. 5C are diagrams showing scattergrams and areas used in the first analysis process according to the embodiment.

In step S101, the processing unit 81 develops the scattergram 210 shown in FIG. 5B for all the tangible components for which parameters were calculated in step S14 of FIG. 4 on the basis of the first measurement sample, and extracts the tangible components in the area 211 from the scattergram 210. The horizontal axis and the vertical axis of the scattergram 210 are FLHP and FSCP, respectively. Region 211 is a region containing fat particles. Since fat particles do not have nucleic acids, fluorescence hardly occurs from fat particles. Therefore, the region 211 containing fat particles is set near the left end of the scattergram 210.

Here, the urine sample may also include small yeast-like fungi and bacteria such as unconnected cocci. These yeast-like fungi and bacteria can overlap fat particles in the scattergram 220 when plotted in the scattergram 220 described below with reference to FIG. 5C. On the other hand, although yeast-like fungi and bacteria bind with nucleic acid binding dye due to having a nucleic acid, fat particles which do not have a nucleic acid do not bind to a nucleic acid binding dye. Therefore, when FLHP is used as a parameter reflecting the intensity of a signal based on fluorescence, yeast-like fungi and bacteria can be excluded from the detection target of fat particles. That is, since yeast-like fungi and bacteria are distributed on the right side of the region 211 in the scattergram 210 shown in FIG. 5B, yeast-like fungi and bacteria can be excluded by extracting the solid components in the region 211. In this way fat particles can be detected more accurately in step S103 to be described later.

Figure 5C:
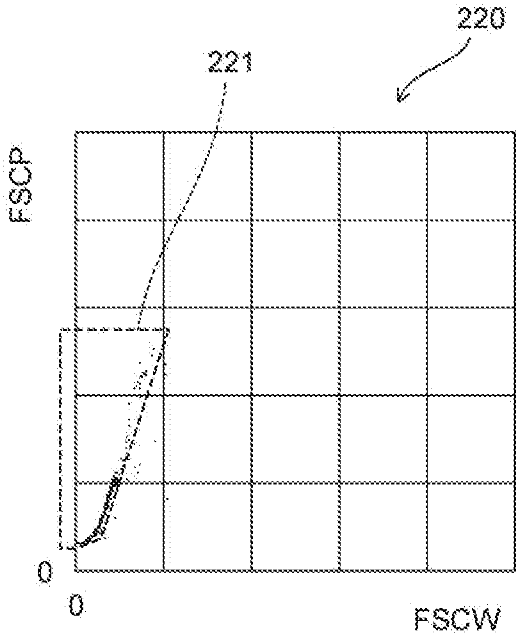

Then, in step S102, the processing unit 81 develops the tangible components extracted in step S101 into the scattergram 220 shown in FIG. 5C, and extracts the tangible components in the area 221 from the scattergram 220. The horizontal axis and the vertical axis of the scattergram 220 are FSCW and FSCP, respectively. The region 221 is a region corresponding to fat particles.

Here, since the fat particles are spherical, the relationship shown in the following formula (1) can be defined between FSCW based on fat particles and FSCP using a predetermined coefficient n.

$$FSCP=n\cdot(FSCW)^2 \quad (1)$$

In the case of fat particles, the coefficient n of the above formula (1) does not vary for each fat particle but is substantially constant. Therefore, the fat particles are distributed on the quadratic curve 222 in the scattergram 220 as shown in FIG. 6A. Other tangible components are substantially undistributed on the left side of the quadratic curve 222. For the above reasons, the region 221 corresponding to fat particles is set so as to include the quadratic curve 222 and the region on the left side of the quadratic curve 222, as shown in FIG. 6A.

Since the fat particles are substantially undistributed to the left side of the quadratic curve 222, the region 221 may be set along the quadratic curve 222 as shown in FIG. 6B. The horizontal axis of the scattergram 220 also may be SSCW instead of FSCW, and the vertical axis of the scattergram 220 is set to FSCP or, alternatively, SSCP may be used. However, since FSCW and FSCP more appropriately reflect the shape of fat particles, it is preferable that the horizontal axis and the vertical axis of the scattergram 220 are FSCW and FSCP, respectively.

Returning to FIG. 5A, the processing unit 81 detects the tangible components extracted in step S102 as fat particles in step S103. In step S103, the processing unit 81 also counts the detected fat particles and acquires the number of fat particles. The number of fat particles obtained in step S103 is the number per unit volume of the urine sample or the measurement sample. The number of the tangible components acquired in the second analysis process, the third analysis process, and the fourth analysis process shown below is also the number per unit volume of the urine sample or the measurement sample. Note that the number of the tangible components is not limited to the number per unit volume but may be the number of the tangible components in the target area of the scattergram.

In preparing the first measurement sample as described above, erythrocytes capable of generating a detection signal similar to fat particles are hemolyzed. Therefore, red blood cells are not substantially distributed in the area 211 of the scattergram 210 and the area 221 of the scattergram 220. Accordingly, detection of erythrocytes as fat particles can be suppressed. Since the fat particles are spherical, the relationship shown in the above formula (1) also can be defined between intensity and width in the signal of forward scattered light based on fat particles, and fat particles can be accurately detected by considering the tangible components in region 221 which was set based on this relationship as fat particles. Since the first measurement sample is flowed through the flow cell 41 and measured, it is possible to properly obtain the detection signal of fat particles and to suppress detection omission of fat particles even if the specific gravity of the fat particles is small. Hence, according to the urine analyzer 10, it is possible to accurately detect fat particles. The detection result of fat particles also can be used for diagnosis of kidney disease and the like.

In the explanation of the first analysis process, a scattergram is generated for convenience, and a region corresponding to the targeted tangible component is set in the generated scattergram. However, generation of a scattergram and setting of a region are not necessarily performed, and tangible components included in a region of a scattergram may be extracted and counted by data processing. Similarly in the second analysis process, the third analysis process, and the fourth analysis process described below, scattergram generation and area setting are not necessarily performed, and the tangible components included in a region of the scattergram also may be extracted and counted by data processing.

In the detection of fat particles in step S103, obtaining the number of fat particles may not always be necessary, and only the presence or absence of fat particles may be obtained based on the extracted fat particles. Similarly, with respect to other tangible components such as erythrocytes as described below, obtaining the number of tangible components in the detection step may not always be necessary, and only the presence or absence of a tangible component may be obtained based on the extracted tangible components.

Figure 7:
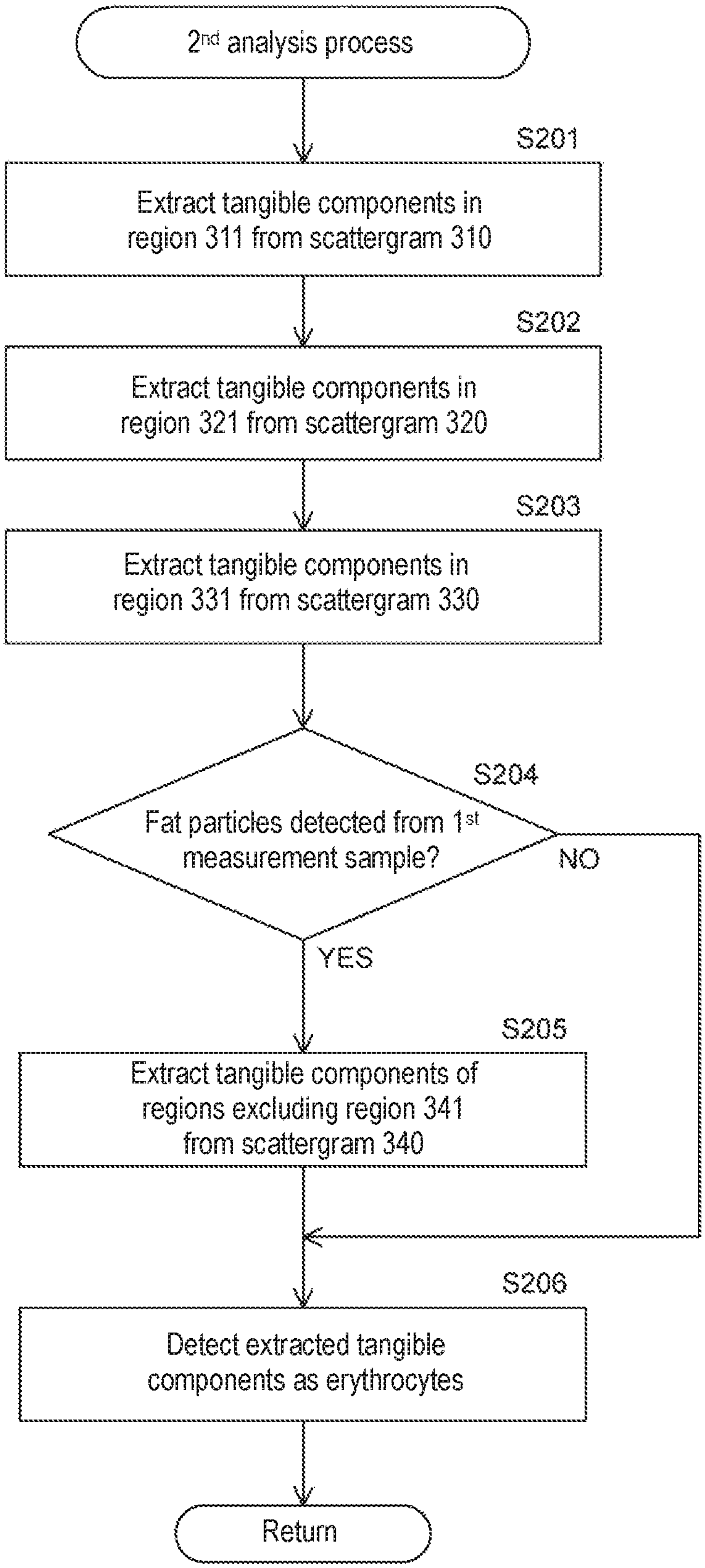
FIG. 7 is a flowchart showing a second analysis process according to the embodiment.

The second analysis process will be described with reference to FIG. 7.

Figure 8A:
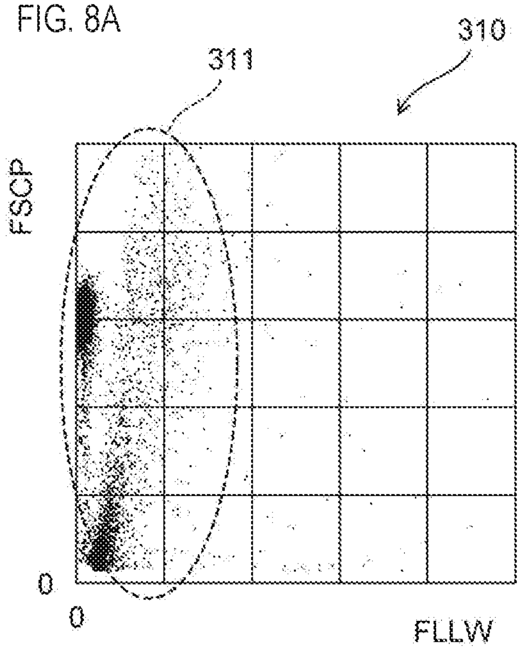
FIG. 8A to FIG. 8C are diagrams showing scattergrams and regions used in the first analysis process according to the embodiment.

In step S201, the processing unit 81 develops all the tangible components for which the parameters were calculated in step S19 in FIG. 4 based on the second measurement sample into the scattergram 310 shown in FIG. 8A, and extracts the tangible components in the region 311 from the scattergram 310. The horizontal axis and the vertical axis of the scattergram 310 are FLLW and FSCP, respectively. Region 311 is a region including erythrocytes. The tangible components other than tangible components of combined erythrocytes and crystals are removed by extracting the tangible components in region 311.

Figure 8B:
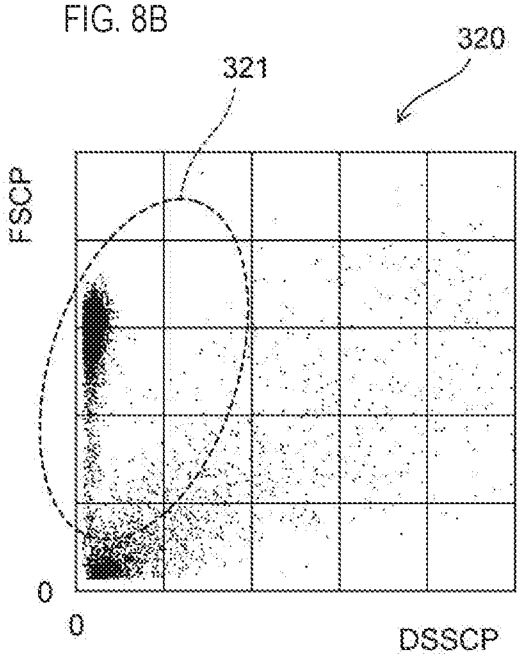

Then, in step S202, the processing unit 81 expands the tangible components extracted in step S201 into the scattergram 320 shown in FIG. 8B, and extracts the tangible components in area 321 from the scattergram 320. The horizontal axis and the vertical axis of the scattergram 320 are DSSCP and FSCP, respectively. Region 321 is a region including erythrocytes. Note that since the crystals are distributed on the right side of the region 321 in the scattergram 320, crystals are removed by extracting the tangible components in the region 321.

Figure 8C:
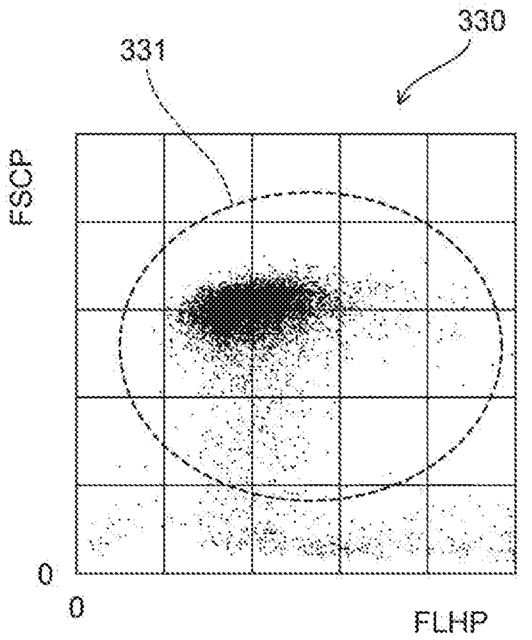

Then, in step S203, the processing unit 81 develops the tangible components extracted in step S202 into a scattergram 330 shown in FIG. 8C, and extracts the tangible components in area 331 from the scattergram 330. The horizontal axis and the vertical axis of the scattergram 330 are FLHP and FSCP, respectively. Region 331 is a region including erythrocytes. Erythrocytes and the like having inappropriate shapes are removed by extracting the tangible components in the region 331.

Then, in step S204, the processing unit 81 determines whether fat particles were detected from the first measurement sample. Specifically, the processing unit 81 determines whether the number of fat particles counted in the first analysis process is larger than a predetermined threshold value th. In this case, the threshold value th is set to be approximately the same as the number of the tangible components in the region 221 of the scattergram 220 counted in the first analysis process when a urine sample does not contain fat particles is measured. The threshold value th is set to, for example, 10 particles/pt. The threshold value th that has been set in this manner is stored in the storage unit 82 in beforehand. Therefore, when it is determined that the number of fat particles counted in the first analysis process in step S204 is larger than the threshold th, it is considered that fat particles are actually present in the urine sample, and determined that fat particles have been detected from the first measurement sample. On the other hand, if it is determined that the number of fat particles counted in the first analysis process in step S204 is equal to or smaller than the threshold th, it is considered that fat particles are not present in the urine sample, and it is determined that fat particles have not been detected from the first measurement sample.

Note that when the presence or absence of fat particles is acquired instead of the number of fat particles in the first analysis process, the processing unit 81 determines "YES" in step S204 when it is determined that there are fat particles in the first analysis process, and determines "NO" when it is determined that there are no fat particles in the first analysis process.

When it is determined in step S204 that fat particles have been detected from the first measurement sample, in step S205, the processing unit 81 converts the tangible components extracted in step S203 into scattered particles shown in FIGS. 9A and 9B Gram 340 and extracts the tangible components of the region excluding the region 341 in step S205. The horizontal axis and the vertical axis of the scattergram 340 are FSCW and FSCP. The entire area of the scattergram 340 is the occurrence range of the erythrocyte-containing tangible component in the second measurement sample, and the area 341 is the occurrence range of fat particles in the second measurement sample. Note that FIG. 9A is a scattergram 340 in the case of a urine sample in which fat particles appear and erythrocytes do not appear, and FIG. 9B shows a scattergram 340 in which fat cells do not appear and erythrocytes appear in the urine sample in scattergram 340.

Here, when fatty particles are included in the first measurement sample as described above, the fat particles are as shown in FIG. 6A distributed on the quadratic curve 222 shown in FIG. 6A since the relationship between FSCW and FSCP based on fat particles is defined by the above formula (1). Therefore, the fat particles contained in the second measurement sample are also distributed on the quadratic curve in the scattergram 340 of FIGS. 9A and 9B. The region 341 is set similarly to the region 221 of FIG. 6A. That is, the region 341 includes a quadratic curve in which fat particles contained in the second measurement sample are distributed, and is set to include the region on the left side of the quadratic curve. Hence, when the tangible components of the region excluding the region 341 are extracted from the scattergram 340 in step S205, the extracted tangible components are those from which fat particles have been removed.

Note that the horizontal axis of the scattergram 340 may be SSCW instead of FSCW and the vertical axis of the scattergram 340 may be SSCP instead of FSCP. However, as in the case of the scattergram 220, since FSCW and FSCP more appropriately reflect the shape of fat particles, the horizontal axis and the vertical axis of the scattergram 340 are preferably FSCW and FSCP, respectively.

Then, in step S206, the processing unit 81 detects the tangible components extracted in the preceding stage as erythrocytes. More specifically, when it is determined that fat particles are present in the urine sample and step S205 is executed, the processing unit 81 detects the tangible components extracted in step S205 as erythrocytes. On the other hand, if it is determined that fat particles are not present in the urine sample and step S205 is not executed, the processing unit 81 detects the tangible components extracted in step S203, in other words, the tangible components of the entire area of the scattergram 340, as erythrocytes. In step S206, the processing unit 81 also counts the detected erythrocytes and acquires the number of erythrocytes. Thus, according to the embodiment, it is possible to accurately detect erythrocytes which are extremely effective for determining the possibility of the morbidity of the kidney disease.

When the processing unit 81 detects the tangible components in the area 331 of the scattergram 330 as erythrocytes in step S203 and determines that the number of fat particles is larger than the threshold th in step S204, correction may be performed to remove the tangible components in the area 341 from the erythrocytes acquired in step S203.

FIG. 9A is a scattergram 340 in the case of a urine sample in which fat particles appeared and no erythrocytes appeared, and FIG. 9B is a scattergram 340 in the case of a urine sample in which erythrocytes appeared without appearance of fat particles. The presence or absence of appearance of fat particles in the urine samples of FIGS. 9A and 9B was determined based on whether the number of fat particles counted in the first analysis process was larger than the threshold th. The presence or absence of erythrocytes on urine samples in FIGS. 9A and 9B was determined based on whether the number of erythrocytes visually observed by microscope was larger than a predetermined value. The urine sample of FIG. 9A is a urine sample determined as having fat particles or not having erythrocytes based on such determination. The urine sample of FIG. 9B is a urine sample determined as not having fat particles and having erythrocytes based on such judgment.

Considering the determination regarding the urine sample, it is understood that the fat particles are distributed in the region 341 of FIG. 9A, and the erythrocytes are distributed in the region 341 of FIG. 9B. In this way, erythrocytes and fat particles may be distributed in the region 341 depending on the amount of fat particles and erythrocytes contained in the urine sample.

In the case of FIG. 9A, the tangible component in the area excluding the area 341 from the scattergram 340 is detected as erythrocytes since it is determined that the number of fat particles counted in the first analysis process is larger than the threshold th. In this case, detection of fat particles as erroneous erythrocytes is suppressed since fat particles distributed in the region 341 in FIG. 9A are excluded. Hence, it is possible to improve the accuracy of the detection result of erythrocytes by correcting the detection result of erythrocytes based on the counting result of fat particles. Since fat particles tend to appear in urine samples collected from patients with kidney disease, false positives also are easily generated in which erythrocyte detection results are positive even though erythrocytes are not mixed in the urine sample. However, when the detection result of erythrocytes is corrected, it is possible to suppress false positives in which the detection result of erythrocytes is positive even in the case of urine samples containing fat particles.

On the other hand, in the case of FIG. 9B, the tangible component of the entire region of the scattergram 340 is detected as erythrocytes since it is determined that the number of fat particles counted in the first analysis process is equal to or less than the threshold th. In this case, the erythrocytes distributed in the region 341 in FIG. 9B are not excluded, so that the erythrocytes can be properly detected.

Note that it is considered that fat particles are contained in the same ratio in the first portion of the urine sample as the source of the first measurement sample and the second portion of the urine sample as the source of the second measurement sample, respectively. Therefore, the number of fat particles included in the second measurement sample can be calculated by calculating the ratio of fat particles contained in the first measurement sample and applying the calculated ratio to the second measurement sample. In this case, the number of erythrocytes contained in the second measurement sample also may be obtained by performing correction to divide the calculated number of fat particles included in the second measurement sample from the number of the characteristic components of the entire region of the scattergram 340.

Figure 10A:
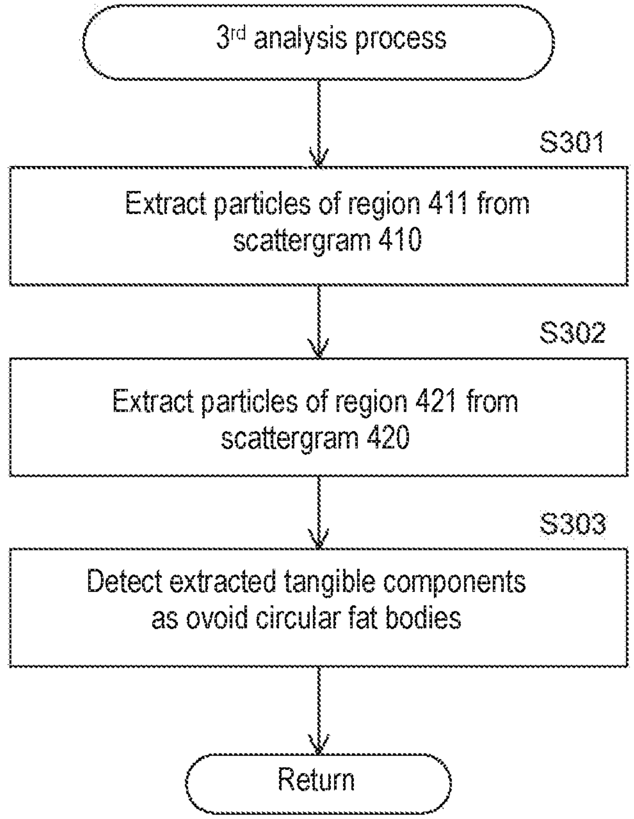
FIG. 10A is a flowchart showing a third analysis process according to the embodiment.

The third analysis process will be described with reference to FIG. 10A.

Figure 10B:
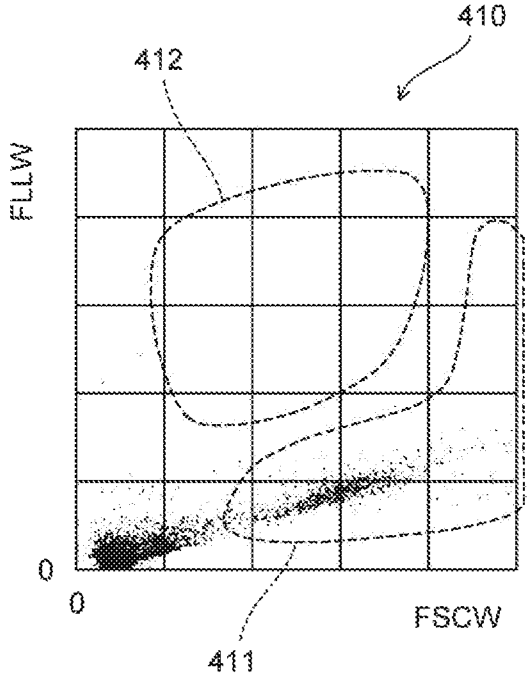
FIG. 10B and FIG. 10C are diagrams showing scattergrams and regions used in the third analysis process according to the embodiment.

In step S301, the processing unit 81 develops the scattergram 410 shown in FIG. 10B for all the tangible components for which parameters were calculated in step S14 of FIG. 4 on the basis of the first measurement sample, and extracts the tangible components in the area 410 from the scattergram 411. The horizontal axis and the vertical axis of the scattergram 410 are FSCW and FLLW, respectively. Region 411 is a region corresponding to all epithelial cells, and region 412 is a region corresponding to casts. The tangible components distributed around the origin of the scattergram 410 also are small blood cells, bacteria and the like.

Figure 10C:
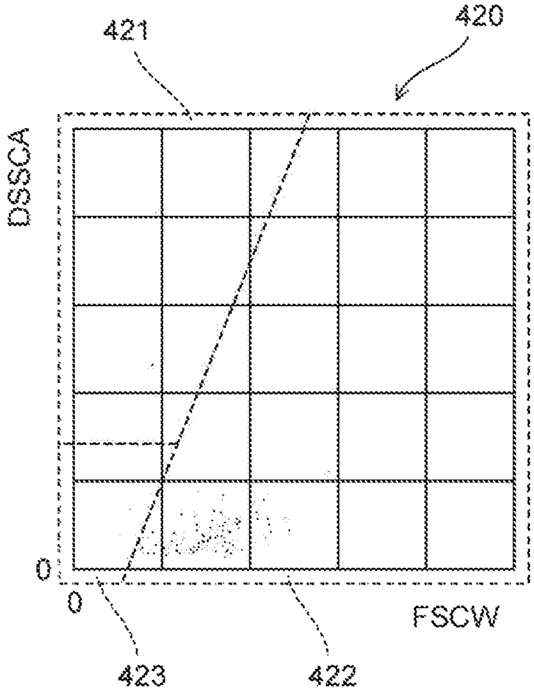

Then, in step S302, the processing unit 81 develops the scattergram 420 shown in FIG. 10C for the tangible components extracted in step S301, and extracts the tangible components in the area 421 from the scattergram 420. The horizontal axis and the vertical axis of the scattergram 420 are FSCW and DSSCA, respectively. The region 421 is a region corresponding to the ovoid circular fat body, the region 422 is a region corresponding to squamous epithelial cells, and the region 423 is a region corresponding to renal tubular epithelial cells.

Here, the DSSCA on the vertical axis indicates the ratio of the light component in the polarization direction perpendicular to the polarization direction before being irradiated on the first measurement sample, among the side scattered light given off from the particle. For this reason, ovoid circular fat bodies, which are generally considered to contain many components which disrupt the initial polarization state, are distributed in a region where the DSSCA value is large compared to squamous epithelial cells and tubular epithelial cells. FSCW on the horizontal axis also shows the width of the tangible component. Therefore, squamous epithelial cells, which are generally considered to be wider than tubular epithelial cells and ovoid circular fat bodies, are distributed in a region where the value of FSCW is large. Tubular epithelial cells, which are not usually contained in many components that disrupt the initial polarization state compared to ovoid fat bodies and are generally considered to be smaller in width than squamous epithelial cells, also are distributed in the region of small values for FSCW and DSSCA.

Then, in step S303, the processing unit 81 detects the tangible component extracted in step S302 as an ovoid circular fat body. In step S303, the processing unit 81 also counts the detected ovoid circular fat bodies to acquire the number of ovoid circular fat bodies. According to the embodiment, ovoid circular fat bodies which are effective for determining the possibility of nephrotic syndrome or chronic nephritis can be detected.

In step S303, the processing unit 81 also detects squamous epithelial cells and renal tubular epithelial cells in addition to detecting the ovoid circular fat bodies. More specifically, the processing unit 81 extracts the tangible components in the areas 422 and 423 of the scattergram 420, and detects the extracted tangible components as squamous epithelial cells and tubular epithelial cells, respectively. Then, the processing unit 81 acquires the number of squamous epithelial cells and number of renal tubular epithelial cells.

Note that a fat column may be distributed in a region where the values of both FSCW and DSSCA are large in scattergram 420. Accordingly, in step S303, it is possible to extract the tangible components in the region where the values of both FSCW and DSSCA are large, and detect the extracted tangible components as fat casts. When fat cells such as ovoid fat bodies and fat columns are detected in this way, it becomes possible to determine the possibility of morbidity with kidney disease together with fat particles and erythrocytes.

The fourth analysis process will be described with reference to FIGS. 11A to 11E. In the fourth analysis process, the scattergrams shown in FIGS. 11A to 11E are generated, various tangible components are detected, and the number of various tangible components is obtained.

Figure 11A:
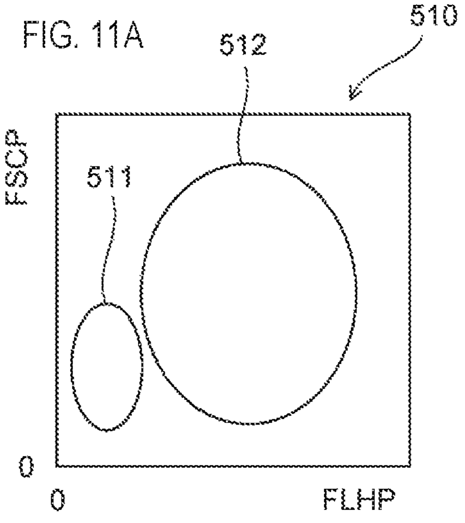
FIG. 11A to FIG. 11E are diagrams showing scattergrams and regions used in a fourth analysis process according to the embodiment.

The scattergram 510 shown in FIG. 11A is a scattergram with two axes of FLHP and FSCP calculated in step S19 of FIG. 4 based on the second measurement sample. Regions 511 and 512 are regions corresponding to crystals and erythrocytes, respectively. In the fourth analysis process, the tangible component in the region 511 is detected as a crystal.

Although it is possible to detect erythrocytes using region 512, the fat particles are distributed in the region 512 when the urine sample contains fat particles. Therefore, in consideration of the possibility that fat particles are contained in the urine sample, detection of erythrocytes is preferably performed as shown in the second analysis process in FIG. 7. Crystals also may be detected using DSSCP. For example, in the scattergram 320 of FIG. 8B a tangible component distributed in a region on the right side of the region 321 may be detected as a crystal.

Figure 11B:
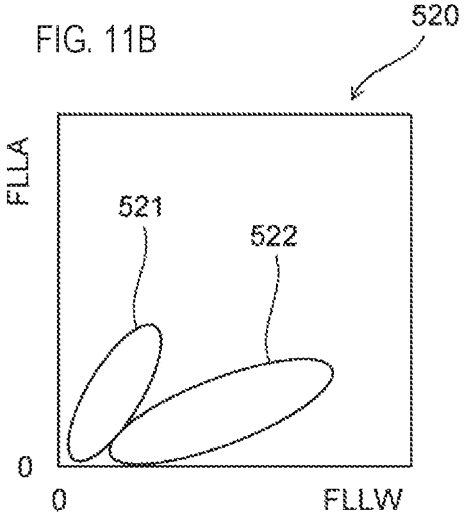

The scattergram 520 shown in FIG. 11B is a scattergram with two axes of FLLW and FLLA calculated in step S19 of FIG. 4 based on the second measurement sample. The regions 521 and 522 are regions corresponding to casts and mucous threads, respectively. In the fourth analysis process, the tangible components in the area 521 are detected as casts, and the tangible components in the area 522 are detected as mucous threads.

Figure 11C:
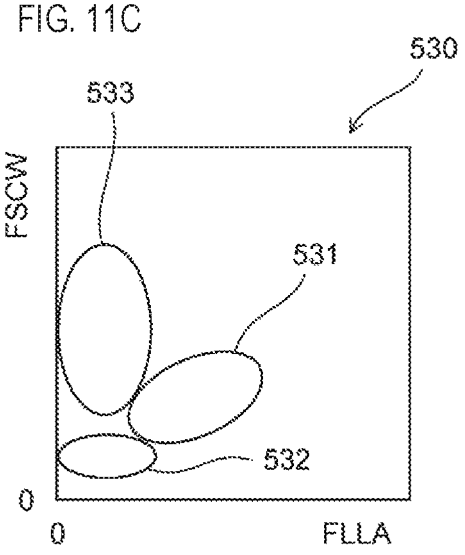

The scattergram 530 shown in FIG. 11C is a scattergram with two axes of FLLA and FSCW calculated in step S14 of FIG. 4 based on the first measurement sample. Regions 531 to 533 are regions corresponding to atypical cells, leukocytes, and epithelial cells, respectively. In the fourth analysis process, the tangible components in the area 531 are detected as heterotypic cells, the tangible components in the area 532 are detected as leukocytes, and the tangible components in the area 533 are detected as epithelial cells.

Figure 11D:
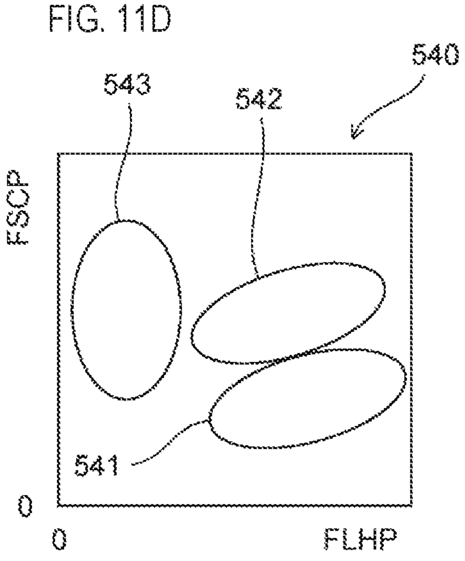

The scattergram 540 shown in FIG. 11D is a scattergram with two axes of FLHP and FSCP calculated in step S14 of FIG. 4 based on the first measurement sample. Regions 541 to 543 are regions corresponding to sperm, fungus, and *trichomonas*, respectively. In the fourth analysis process, the tangible components in the area 541 are detected as spermatozoa, the tangible components in the area 542 are detected as fungi, and the tangible components in the area 543 are detected as *Trichomonas*.

Figure 11E:
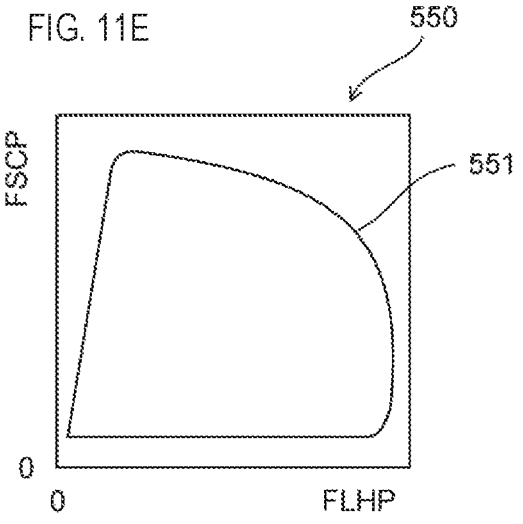

A scattergram 550 shown in FIG. 11E is a scattergram with two axes of FLHP and FSCP calculated in step S16 of FIG. 4 based on the first measurement sample. Region 551 is a region corresponding to bacteria. In the fourth analysis process, the tangible component in the region 551 is detected as bacteria.

According to the urine analyzer 10 described above, crystals, casts, mucous yarns, atypical cells, leukocytes, epithelial cells, sperm, fungi, *trichomonas* and bacteria can be detected in step S23 in addition detecting fat particles, erythrocytes, and ovoid circular fat bodies in steps S20 to S22. That is, since these tangible components can be detected by one urine analyzer 10, the operator does not need to selectively use a plurality of urine analyzers.

Figure 12:
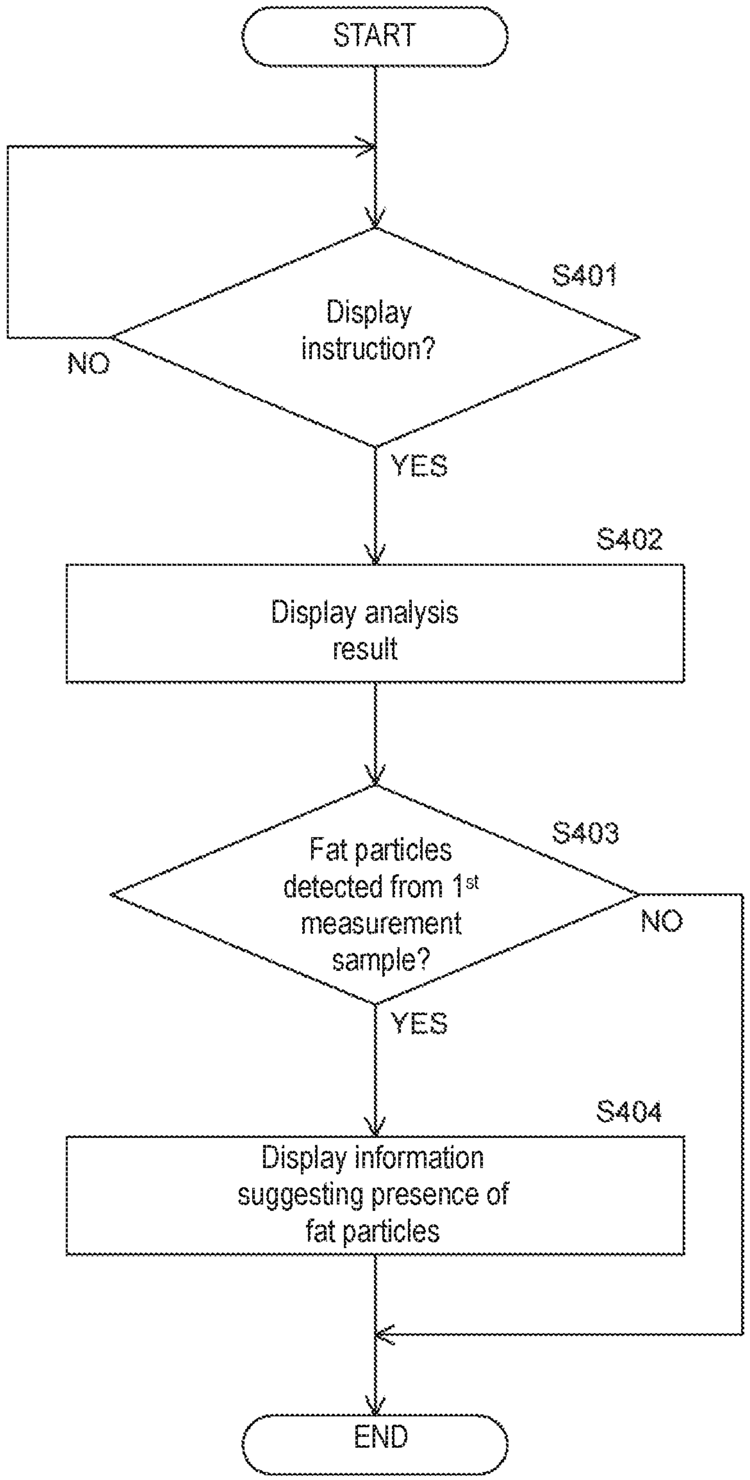
FIG. 12 is a flowchart showing a process for displaying a result of analysis by a urine analyzer according to an embodiment.

Next, a process for displaying the result of analysis by the urine analyzer 10 will be described with reference to FIG. 12.

In step S401, the processing unit 81 determines whether a display instruction has been received from the operator via the input unit 84. Upon receipt of the display instruction, in step S402, the processing unit 81 displays the detection result of the tangible components in the urine sample acquired in the analysis process in steps S20 to S23 in FIG. 4 on the display unit 83. Specifically, the processing unit 81 displays on the display unit 83 a screen 600 including the number of each of the tangible components. The screen 600 will be described later with reference to FIG. 13. Note that when the presence of a tangible component is acquired in the analysis process, the presence of the tangible component is displayed on the screen 600 in step S402.

Then, in step S403, the processing unit 81 determines whether fat particles are detected from the first measurement sample. In other words, the processing unit 81 determines whether the erythrocyte detection result has been corrected based on the counting result of fat particles. The determination in step S403 is the same as the determination in step S204 in the second analysis process in FIG. 7. That is, the processing unit 81 determines whether the number of fat particles obtained in the first analysis process is larger than the threshold th.

When it is determined that fat particles are detected from the first measurement sample, the processing unit 81 displays information indicating the presence of fat particles together with the detection result of erythrocytes obtained in the second analysis processing on the display unit 83 in step S404. More specifically, the processing unit 81 displays information indicating the presence of fat particles on the screen 600 displayed on the display unit 83 in step S402. In this way it is possible to notify the operator that the fat particles interfered in the detection of erythrocytes.

Figure 13:
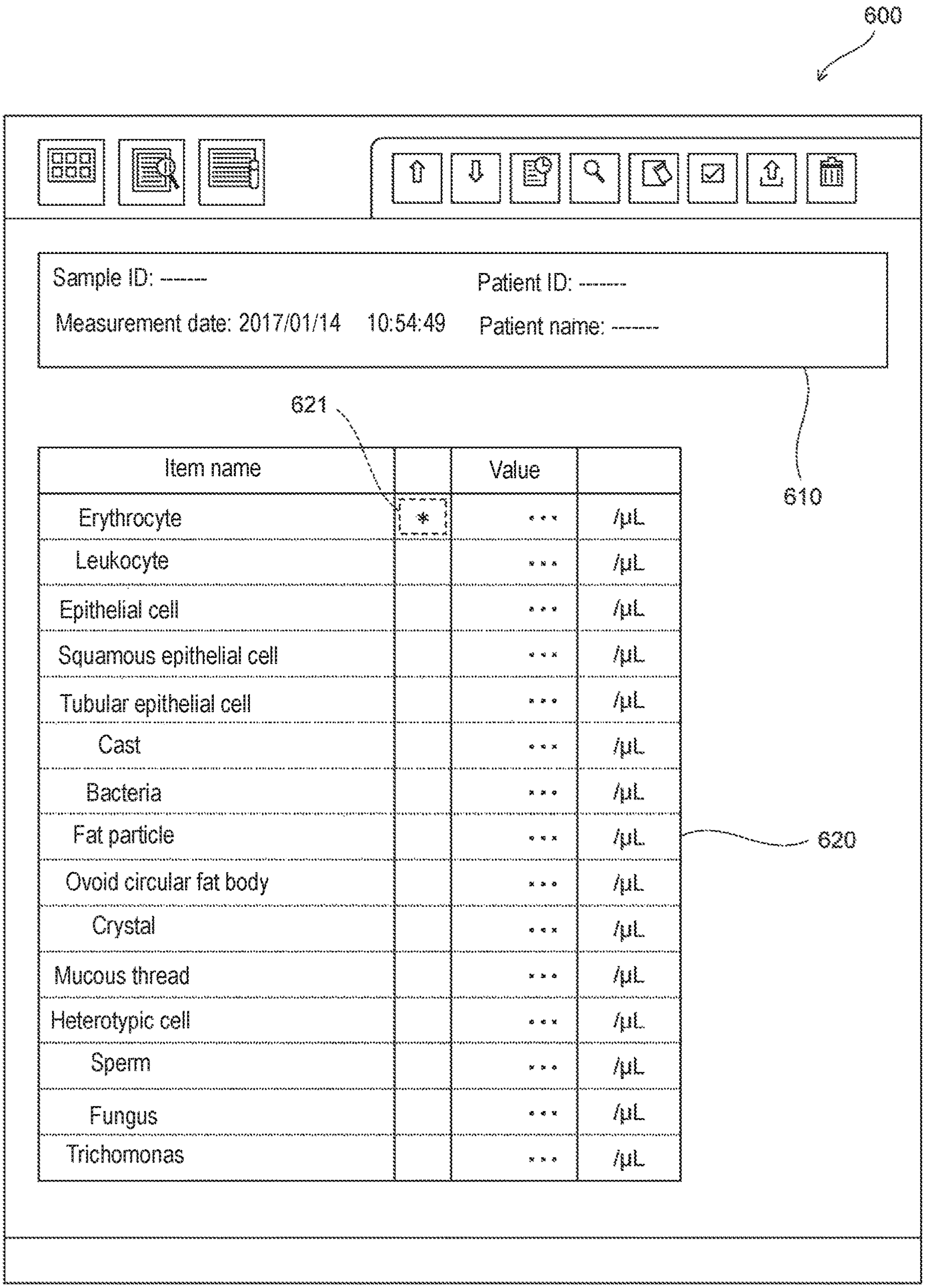
FIG. 13 is a diagram schematically showing a screen displayed on a display unit according to the embodiment.

As shown in FIG. 13, the screen 600 includes an area 610 and a list 620. In the region 610, information is displayed related to the urine sample which is the basis of the analysis result displayed on the screen 600. Information on the urine sample includes the ID of the urine sample, the ID and the name of the patient from whom the urine sample was collected, and the measurement date and time of the urine sample. In the list 620, the number of the tangible components acquired by the analysis process in steps S20 to S23 in FIG. 4 is displayed as the detection result. When it is determined that fat particles are detected from the first measurement sample as exemplified in FIG. 13, a character string 621 also is displayed in the erythrocyte item of the list 620 as information suggesting the presence of fat particles. As shown in FIG. 13, the character string 621 is, for example, "*". The character string 621 may be "with correction" or the like.

When a detection result including the presence or absence of a tangible component and the counting result is displayed, the operator can use the detection result of each tangible component for various diagnoses. Specifically, the operator can diagnose kidney disease by referring to the detection result of fat particles. The operator also can more accurately diagnose kidney disease by referring to the detection results of erythrocytes and ovoid circular fat bodies.

VERIFICATION OF EMBODIMENTS

Next, the inventors counted erythrocytes based on the method of the embodiments and comparative examples regarding actual urine samples, and verified the detection accuracy of erythrocytes according to the embodiments. In the comparative example, steps S204 and S205 are omitted in the second analysis process of FIG. 7. That is, in the comparative example, the tangible components in the region 331 of the scattergram 330 shown in FIG. 8C were counted as erythrocytes.

FIG. 14A and FIG. 14B are the results of counting erythrocytes based on the methods of the comparative example and the embodiment for 127 urine samples. These urine samples were collected mainly in urinary specimens suspected of containing fat particles. In this verification, the erythrocyte count based on microscopic examination was performed in addition to counting based on the comparative example and the embodiment. In counting erythrocytes by microscope, the inventors placed the 127 urine samples on a slide without centrifugation and observed the urine sample placed on the slide with a microscope to count erythrocytes. In the verification described below, it was assumed that the number of erythrocytes obtained based on the microscope is the number of actual erythrocytes, and the detection accuracy of erythrocytes according to the comparative example and the embodiment was verified by comparing the number of erythrocytes obtained by the methods of the comparative example and the embodiment with the number of erythrocytes obtained based on the microscope.

In FIGS. 14A and 14B, the rank of the erythrocyte count is 0, 1 to 5, 6 to 10, 11 to 15, more than 15 for the three methods of the comparative example, the embodiment and the microscope, and the numbers of corresponding urine samples are shown. The fields surrounded by a solid line represents the number of urine samples when the rank of the erythrocyte count based on the method of the comparative example or the embodiment coincides with the rank of the erythrocyte count based on the microscope. The fields surrounded by a broken line represent the number of urine samples when the rank of the erythrocyte count based on the method of the comparative example or the embodiment deviates from the rank of the erythrocyte count based on the microscope by +1 rank or −1 rank.

In the case of the comparative example as shown in FIG. 14A, the number of urine samples surrounded by the solid line and the broken line was 45. In the case of the comparative example, therefore, the ratio of the number of urine samples whose rank of erythrocyte count coincides with the microscope within ±1 rank to the total number of urine samples, that is, ±1 rank coincidence ratio, is 45/127=35.4%. On the other hand, in the case of the embodiment, the number of urine samples surrounded by the solid line and the broken line was 74 as shown in FIG. 14B. Therefore, in the case of the embodiment, the coincidence ratio of ±1 rank was 74/127=58.3%.

In the verification shown in FIGS. 14A and 14B described above, it was found that the counting result of the embodiment approaches the counting result of the microscope more than the counting result of the comparative example. Therefore, erythrocytes can be counted more accurately according to the embodiment than in the comparative example.

FIGS. 15A and 15B are the results of counting erythrocytes based on the methods of the comparative example and the embodiment for 248 general urine samples. Even in this verification, the erythrocyte count based on the microscope was performed in addition to the counts based on the comparative example and the embodiment. In counting erythrocytes by microscope, the inventors centrifuged these 248 urine samples, placed the urine sample on a calculation board and observed the urine sample placed on the calculation board with a microscope to count erythrocytes. In the verification described below, it was assumed that the number of erythrocytes obtained based on the microscope is the number of actual erythrocytes, and the detection accuracy of erythrocytes according to the comparative example and the embodiment was verified by comparing the number of erythrocytes obtained by the methods of the comparative example and the embodiment with the number of erythrocytes obtained based on the microscope.

In FIGS. 15A and 15B, the rank of the erythrocyte count is 0, 1 to 4, 5 to 9, 10 to 19, 20 to 29, 30 to 49, 50 to 99, more than 100, and the number of corresponding urine samples is shown. The fields surrounded by a solid line represents the number of urine samples when the rank of the erythrocyte count based on the method of the comparative example or the embodiment coincides with the rank of the erythrocyte count based on the microscope. The fields surrounded by a broken line represent the number of urine samples when the rank of the erythrocyte count based on the method of the comparative example or the embodiment deviates from the rank of the erythrocyte count based on the microscope by +1 rank or −1 rank.

As shown in FIG. 15A, in the case of the comparative example the number of urine samples surrounded by the solid line and the broken line was 222. Therefore, in the case of the comparative example, the coincidence ratio of ±1 rank was 222/248=89.5%. On the other hand, in the embodiment the number of urine samples surrounded by the solid line and the broken line was 226 as shown in FIG. 15B. Therefore, in the case of the embodiment the ±1 rank coincidence ratio was 226/248=91.1%.

In the verification shown in FIGS. 15A and 15B as shown in FIG. 15B, it also was found that the count result of the embodiment approaches the count result of the microscope closer than the count result of the comparative example. Therefore, erythrocytes can be counted more accurately according to the embodiment than in the comparative example.

What is claimed is:

1. A urine analyzer comprising:

a sample preparation unit configured to mix a urine sample with a hemolytic agent to prepare a measurement sample;

a flow cell that receives the measurement sample;

a light source configured to irradiate light on the measurement sample flowing through the flow cell;

a light receiving unit configured to receive scattered light given off from the measurement sample in response to the irradiated light, and to output a scattered light signal; and an analysis unit that detects fat particles that are aggregates of fat molecules existing extracellularly in the measurement sample using a parameter that reflects an intensity of the scattered light signal output by the light receiving unit and a parameter that reflects a width of the scattered light signal.

2. The urine analyzer according to claim 1, wherein the light receiving unit receives forward scattered light as scattered light given off from the measurement sample.

3. The urine analyzer according to claim 1, wherein the sample preparation unit prepares the measurement sample by also mixing the urine sample with a staining agent containing a nucleic acid binding dye that binds to nucleic acid and emits fluorescence via the light from the light source;

the light receiving unit receives the fluorescence given off from the measurement sample by the irradiation of the light; and the analysis unit detects fat particles in the measurement sample based on the fluorescence received by the light receiving unit.

4. The urine analyzer according to claim 1, wherein the analysis unit counts the detected fat particles.

5. The urine analyzer according to claim 1, further comprising:

a stirring unit for mixing the urine sample in a sample container;

a suction unit that suctions the urine sample from the sample container after the urine sample is mixed by the stirring unit; and the sample preparation unit prepares the measurement sample from the urine sample suctioned by the suction unit.

6. The urine analyzer according to claim 1, wherein the sample preparation unit prepares the measurement sample by mixing the hemolytic agent with a part of the urine sample and prepares other measurement sample without hemolyzing erythrocytes from other part of the urine sample;

the light receiving unit receives light given off from the other measurement sample flowing through the flow cell upon irradiation of the light; and the analysis unit detects erythrocytes in the other measurement sample based on the light received by the light receiving unit from the other measurement sample.

7. The urine analyzer according to claim 6, wherein the sample preparation unit prepares the other measurement sample by mixing the other part of the urine sample with another stain containing a cell membrane-bound dye which binds to a cell membrane and emits fluorescence by irradiation of light from the light source;

the light receiving unit receives the fluorescence given off from the other measurement sample by the irradiation of the light; and the analysis unit detects erythrocytes in the other measurement sample based on the fluorescence received by the light receiving unit from the other measurement sample.

8. The urine analyzer according to claim 6, wherein the analysis unit counts erythrocytes in the other measurement sample based on the light received by the light receiving unit from the other measurement sample and the detection result of fat particles obtained from the measurement sample.

9. The urinal analyzer according to claim 8, wherein the light receiving unit receives scattered light given off from the other measurement sample flowing through the flow cell upon irradiation of the light, and outputs a scattered light signal; and the analysis unit, in responsive to a detection of the fat particles from the measurement sample, counts the erythrocytes in the other measurement sample based on an occurrence range of fat particles and an occurrence range of tangible components including the erythrocytes, the occurrence ranges being stipulated by a parameter reflecting the intensity of the scattered light signal obtained from the other measurement sample and a parameter reflecting the width of the scattered light signal obtained from the other measurement sample.

10. The urine analyzer according to claim 9, wherein the analysis unit, in responsive to a detection of the fat particles from the measurement sample, counts, as erythrocytes, the tangible components included in a range generated by excluding the occurrence range of fat particles from the occurrence range of tangible components including erythrocytes.

11. The urine analyzer according to claim 1, further comprising:

a display unit;

wherein the analysis unit displays information suggesting a presence of fat particles and a count result of erythrocytes obtained from the other measurement sample on the display unit, when fat particles are detected from the measurement sample.

12. The urine analyzer according to claim 1, wherein the light source irradiates linearly polarized light on the measurement sample flowing through the flow cell;

the light receiving unit receives depolarized scattered light from the measurement sample; and the analysis unit detects the fat particles in the measurement sample based on the depolarized scattered light received by the light receiving unit from the measurement sample.

13. The urine analyzer according to claim 12, wherein the fat particles comprise ovoid circular fat bodies.

14. The urine analyzer according to claim 1, further comprising:

a display unit;

wherein the analysis unit causes the display unit to display a detection result of tangible components in the urine sample.

15. An urinalysis method comprising:

preparing a measurement sample by mixing hemolytic agent in a urine sample;

flowing the measurement sample into a flow cell;

receiving scattered light given off by irradiating light on the measurement sample flowing through the flow cell; and detecting fat particles that are aggregates of fat molecules existing extracellularly in the measurement sample using a parameter that reflects an intensity of a scattered light signal corresponding to the received scattered light and a parameter that reflects a width of the scattered light signal.

16. A urine analyzer comprising:

a sample preparation unit configured to prepare a measurement sample without hemolyzing erythrocytes from the urine sample;

a flow cell that receives the measurement sample;

a light source configured to irradiate light on the measurement sample flowing through the flow cell;

a light receiving unit configured to receive scattered light given off from the measurement sample in response to the irradiated light, and to output a scattered light signal; and an analysis unit that counts, as erythrocytes, tangible components included in a range generated by excluding, from an occurrence range of tangible components including erythrocytes, a range in which a parameter reflecting the intensity of the scattered light signal and a parameter reflecting the width of the scattered light signal have a predetermined relationship, the occurrence range being prescribed by a parameter reflecting the intensity of the scattered light signal output from the light receiving unit and a parameter reflecting the width of the scattered light signal.

17. The urine analyzer according to claim 16, wherein the range in which the parameter reflecting the intensity of the scattered light signal and the parameter reflecting the width of the scattered light signal have the predetermined relationship is a range in which fat particles appear.

18. The urine analyzer according to claim 16, wherein the sample preparation unit prepares the measurement sample from a part of the urine sample, and prepares other measurement sample by mixing a hemolytic agent with another part of the urine sample;

the light receiving unit receives scattered light given off from the other measurement sample flowing through the flow cell upon irradiation of the light, and outputs a scattered light signal; and the analysis unit counts, as erythrocytes, the tangible components included in the occurrence range of tangible components including erythrocytes when a tangible component is not detected in a range in which the parameter reflecting the intensity of the scattered light signal obtained from the other measurement sample and the parameter reflecting the width of the scattered light signal obtained from the other measurement sample have a predetermined relationship.

19. An urinalysis method comprising:

preparing a measurement sample without hemolyzing erythrocytes in a urine sample;

flowing the measurement sample into a flow cell;

receiving scattered light given off by irradiating light on the measurement sample flowing through the flow cell; and counting, as erythrocytes, tangible components included in a range generated by excluding, from an occurrence range of tangible components including erythrocytes, a range in which a parameter reflecting the intensity of the scattered light signal and a parameter reflecting the width of the scattered light signal have a predetermined relationship, the occurrence range being prescribed by a parameter reflecting the intensity of the scattered light signal output from the light receiving unit and a parameter reflecting the width of the scattered light signal.

20. A urine analyzer comprising:

a sample preparation unit configured to prepare a measurement sample without hemolyzing erythrocytes in a urine sample;

a flow cell that receives the measurement sample;

a light source configured to irradiate light on the measurement sample flowing through the flow cell;

a light receiving unit configured to receive scattered light given off from the measurement sample in response to the irradiated light, and to output a scattered light signal; and an analysis unit that counts, as erythrocytes, tangible components included in a range generated by excluding, from an occurrence range of tangible components including erythrocytes prescribed by parameter obtained from scattered light signals output by the light receiving unit, an occurrence range of fat particles that are aggregates of fat molecules existing extracellularly prescribed by the parameter.

21. An urinalysis method comprising:

preparing a measurement sample without hemolyzing erythrocytes in a urine sample;

flowing the measurement sample into a flow cell;

receiving scattered light given off by irradiating light on the measurement sample flowing through the flow cell; and counting, as erythrocytes, tangible components included in a range generated by excluding, from an occurrence range of tangible components including erythrocytes prescribed by parameter obtained from scattered light signals corresponding to the received scattered light, an occurrence range of fat particles that are aggregates of fat molecules existing extracellularly prescribed by the parameter.

* * * * *